United States Patent
Long et al.

(10) Patent No.: US 8,580,998 B2
(45) Date of Patent: Nov. 12, 2013

(54) PREPARATION OF ALKENES BY MILD THERMOLYSIS OF SULFOXIDES

(75) Inventors: Timothy Edward Long, Athens, GA (US); Sravan Kumar Patel, Andhra Pradesh (IN)

(73) Assignee: University of Georgia Research Foundation, Inc., Athens, GA (US)

( * ) Notice: Subject to any disclaimer, the term of this patent is extended or adjusted under 35 U.S.C. 154(b) by 218 days.

(21) Appl. No.: 13/131,336

(22) PCT Filed: Nov. 17, 2009

(86) PCT No.: PCT/US2009/064708
§ 371 (c)(1),
(2), (4) Date: May 26, 2011

(87) PCT Pub. No.: WO2010/068371
PCT Pub. Date: Jun. 17, 2010

(65) Prior Publication Data
US 2011/0230641 A1    Sep. 22, 2011

Related U.S. Application Data

(60) Provisional application No. 61/121,632, filed on Dec. 11, 2008, provisional application No. 61/139,824, filed on Dec. 22, 2008.

(51) Int. Cl.
*C07C 303/00* (2006.01)
*C07C 321/00* (2006.01)
*C07C 317/00* (2006.01)

(52) U.S. Cl.
USPC .............. 560/149; 568/21; 568/37

(58) Field of Classification Search
None
See application file for complete search history.

(56) References Cited

U.S. PATENT DOCUMENTS
5,401,766 A    3/1995 Geiger et al.

FOREIGN PATENT DOCUMENTS
WO    9915507 A1    4/1999

OTHER PUBLICATIONS

Afzali-Ardakani et al., J. Org. Chem., 1980, 45, 4817-4820.*
Berkowitz et al., Tetrahedron: Asymmetry 17 (2006) 869-882.*
Entwistle et al., J. Am. Chem. Soc., 1962, 84, 866 29-30.*
Yoshimura et al. Bull. Chem. Soc. Jpn., 60, 2491-2496, 1987.*
Database Caplus Chemical Abstracts Service, Columbus, Ohio, US; Database Accession No. 1973:525594, Abstract of Shelton et al., International Journal of Sulfur Chemistry (1973), 3(2), 197-204.*
Database Caplus Chemical Abstracts Service, Columbus, Ohio, US; Database Accession No. 1965:403151, Abstract of NL 6408999 to Shell Internationale Research Maatschappij NV, Feb. 9, 1965.*
Gamble et al., Tetrahedron Letters (1996), 37(41), 7457-7460, p. 7459.*

(Continued)

*Primary Examiner* — Karl J Puttlitz
(74) *Attorney, Agent, or Firm* — Thomas Horstemeyer, LLP

(57) ABSTRACT

Embodiments of this disclosure, among others, encompass methods for generating alkenes under mild thermolytic conditions that can provide almost total conversion of a precursor compound to an alkene without isomerization or the need to chromatographically purify the final product By selectively blocking the amino and carboxy groups of the derivatized amino acid, the methods of the disclosure provide for the synthesis of a peptide having the vinylglycine moiety at either the carboxy or the amino terminus of the peptide The mild conditions for the thermolytic removal of an o-$NO_2$-phenyl substituted aryl group ensure that there is minimal if any damage to thermally sensitive conjugates such as a peptide bearing the vinylglycine The methods of the present disclosure have practical applications for the preparation of unsaturated compounds under mild, thermolytic conditions.

16 Claims, 13 Drawing Sheets

(56) References Cited

OTHER PUBLICATIONS

International Search Report and Written Opinion dated Jul. 12, 2010.
Afzal I-Ardakani, et a., "L-Vinylglycine", J. Org. Chem. vol. 45, pp. 4817-4820, 1980.
Dominguez, et al., "Solid-Phase Synthesis of Substituted Glutamic Acid Derivatives via Michael Addition Reactions," Tetrahedron Lett. vol. 39(15), pp. 2167-2170, 1998.
Berkowitz, et al., "Alpha-Vinylic Amino Acids: Occurrence, Asymmetric Synthesis, and Biochemical Mechanisms," Tetrahedron: Asymmetry Report No. 86, Apr. 4, 2006, pp. 869-882.
Haillnan, et al., "Simple Synthesis of L- and D-Vinylglycine (2-Aminobut-3-enoic Acid) and Related Amino Acids," Chem. Soc. Perkin Trans. 1, 1994, pp. 3537-3543.

\* cited by examiner (a) ONP vs. Phenyl

19h n=3
19i n=8 n=3 (62%)[a]
n=8 (86%)

(b) ONP vs. p-Methylphenyl

19j

20j (87%)

(c) ONP vs. p-Chlorophenyl

19k

20k (74%)

(d) ONP vs. p-Nitrophenyl

19l n=3
19m n=8

20l n=3 (61%)
20m n=8 (64%)

| R | R' | R" | Product |
|---|---|---|---|
| Alkyl, e.g. Me | H | H | e.g. Propylene |
| Phenyl | H | H | Styrene |
| Phenyl | H | Me | β-methyl styrene |
| Phenyl (substituted) | H | H | o, p, m substituted styrene |
| Napthyl | Phenyl | Phenyl (substituted) C₆H₄R'''' R'''' = OH, MeO, BuO, etc | estrogen mimetic |
| Acene (Ac) n= 0, 1, 2 e.g.: 2-Napthyl 2-anthracenyl 2-tetracenyl | H, Me, Halide, OH | Acene (Ac) n= 0, 1, 2 e.g.: 2-Napthyl 2-anthracenyl 2-tetracenyl |  |

PREPARATION OF ALKENES BY MILD THERMOLYSIS OF SULFOXIDES

CROSS REFERENCE TO RELATED APPLICATION

This application claims priority to Preparation of Alkenes by Mild Thermolysis of Sulfoxides," having serial number PCT/US2009/064708, filed on Nov. 17, 2009. This application also claims priority to and benefit of U.S. Provisional Application No. 61/121,632, filed on Dec. 11, 2008, and U.S. Provisional Application No. 61/139,824, filed on Dec. 22, 2008, both of which are incorporated by reference in their entirety.

TECHNICAL FIELD

The present disclosure is generally related to methods of synthesizing alkenes by mild thermolysis of sulfoxides. The present disclosure further relates to methods of synthesizing vinylglycine and compounds, and particularly amino acids and peptides that include a vinylglycine group.

BACKGROUND

Vinylglycine (2-aminobut-3-enoic acid)) (Berkowitz et al., *Tetrahedron: Asym.* (2006) 12: 869) is a natural, non-protein α-amino acid and irreversible inhibitor of enzymes that use pyridoxal phosphate (PLP) as a cofactor, such as a alanine racemase, aspartate aminotransferase, and α-ketoglutarate dehydrogenase (Lacoste et al., (1988) *Biochem. Soc. Trans.* 16: 606; Rando R. R. (1974) *Biochemistry* 13: 3859; Lai & Cooper (1986) *J. Neurochem.* 47: 1376). As a suicide substrate, research has centered on identifying additional natural and synthetic β,γ-olefinic amino acids capable of selectively deactivating enzymes. In addition, protected forms of vinylglycine have been useful in the synthesis of metabotropic glutamate receptors agonists (Selvam et al., (2007) *J. Med. Chem.* 50: 4656) poly-γ-glutamate synthetase inhibitors (Valiaeva et al., (2001) *J. Org. Chem.* 66: 5146), and the antitumor antibiotic (+)-FR900482 (Paleo et al., (2003) *J. Org. Chem.* 68: 130).

Traditionally, the methods of choice to prepare L-vinylglycine have been the pyrolysis of protected methionine sulfoxide (MetO) (Afzali-Ardakani & Rapoport (1980) *J. Org. Chem.* 45: 4817) and thermolysis of aryl selonoxides obtained from either protected L-glutamate (Hanessian & Sahoo (1984) *Tetrahedron Lett.* 25: 1425), L-homoserine (Pellicciari et. al. (1988) *Synth. Commun.* 69: 7982), or L-homoserine lactone (Berkowitz & Smith (1996) *Synthesis* 39). For multi-gram syntheses, the MetO pyrolysis approach is most commonly implemented. However, due to the high vacuum (≤3 mm Hg) and temperature (>150° C.) requirements, isomerization is a consistent problem for the reaction.

The migratory occurrence to the more thermally stable β-methyldehydroalanine is further enhanced by the acidity of the α-proton in N,O-protected forms of vinylglycine. The isomer forms quantitatively in the presence of triethylamine or N-methylmorpholine (Afzali-Ardakani & Rapoport (1980) *J. Org. Chem.* 45: 4817) and it is likewise believed decomposition during silica purification contributes to a optimized yield of 60% (Carrasco et al., (1992) *Org. Synth.* 70: 29).

Because of the difficulty of isolating the α,β-isomer from protected vinylglycines by chromatography and the desire to find a non-pyrolytic large scale approach, it is desirable for alternative sulfinyl substituents that would syn-eliminate at temperatures below 150° C.

SUMMARY

Briefly described, embodiments of this disclosure, among others, encompass methods for generating alkenes under mild thermolytic conditions that can provide almost total conversion of a precursor compound to an alkene without isomerization or the need to chromatographically purify the final product. By selectively blocking the amino and carboxy groups of the derivatized amino acid, the methods of the disclosure provide for the synthesis of a peptide having the vinylglycine moiety at either the carboxy or the amino terminus of the peptide. The mild conditions for the thermolytic removal of an o-NO$_2$-phenyl substituted aryl group ensure that there is minimal if any damage to thermally sensitive conjugates such as a peptide bearing the vinylglycine.

One aspect of the present disclosure, therefore, encompasses methods for synthesizing an alkene under mild thermolytic conditions, the methods comprising: (a) providing a sulfoxide having the formula I:

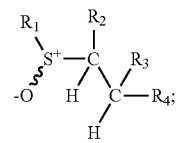

where: $R_1$ is an electron withdrawal group; and $R_2$, $R_3$, and $R_4$ are each independently selected from the group consisting of: H, an alkyl group, an aromatic group, an amino acid, and a peptide; (b) refluxing the compound having formula I in the presence of a non-polar and aprotic solvent, and at a temperature of about 90° C. to about 135° C., thereby generating an alkene; and (c) isolating from the non-polar and aprotic solvent the alkene, wherein the alkene has the formula II:

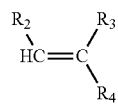

where $R_2$, $R_3$, and $R_4$ can be each independently selected from the group consisting of: H, an aliphatic group, an aromatic group, an amino acid, and a peptide;

In embodiments of this aspect of the disclosure, the electron withdrawing group $R_1$ may be, but is not limited to, an o-nitrophenyl group or a p-nitrophenyl group.

In an especially useful embodiment of the disclosure, the electron withdrawing group $R_1$ is o-nitrophenyl.

Another aspect of the disclosure encompasses method for synthesizing an alkene, comprising: (a) providing a compound having formula III:

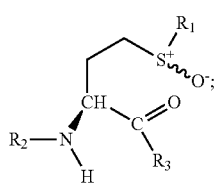

where: $R_1$ is an electron withdrawal group; $R_2$ and $R_3$ can each be individually selected from the group consisting of: H, a removable protecting group, an amino acid and a peptide; and if $R_2$ is an amino acid or a peptide, $R_3$ is a removable protecting group; and if $R_3$ is an amino acid or a peptide, $R_2$ is a removable protecting group; (b) refluxing the compound having formula I in the presence of a non-polar and aprotic solvent, and at a temperature of about 90° C. to about 135° C., thereby generating an alkene; and (c) isolating from the non-polar and aprotic solvent an alkene having formula VI:

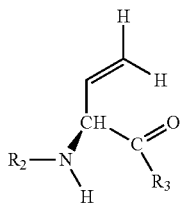

In embodiments of this aspect of the disclosure, the electron withdrawal group $R_1$ can be an aryl group selected from the group consisting of: a benzyl group, a phenyl group, a p-methoxyphenyl group, a p-chlorophenyl group, a p-nitrophenyl group, and an o-nitrophenyl group.

In the embodiments of this aspect of the disclosure, step (b) can further comprise including with the non-polar aprotic solvent a molar excess of sodium acetate.

Still another aspect of the disclosure encompasses sulfoxides having the general formula I:

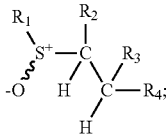

where $R_1$ can be an electron withdrawal group; and $R_2$, $R_3$, and $R_4$ can be each independently selected from the group consisting of: H, an alkyl group, an aromatic group, an amino acid, and a peptide.

Still yet another aspect of the disclosure encompasses compounds having formula III:

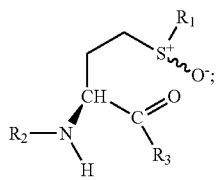

where $R_1$ can be an aryl group selected from the group consisting of: a benzyl group, a phenyl group, a p-methoxyphenyl group, a p-chlorophenyl group, a p-nitrophenyl group, and an o-nitrophenyl group; $R_2$ and $R_3$ can each be individually selected from the group consisting of: H, a removable protecting group, an amino acid and a peptide; and if $R_2$ is an amino acid or a peptide, $R_3$ is a removable protecting group; and if $R_3$ is an amino acid or a peptide, $R_2$ is a removable protecting group.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
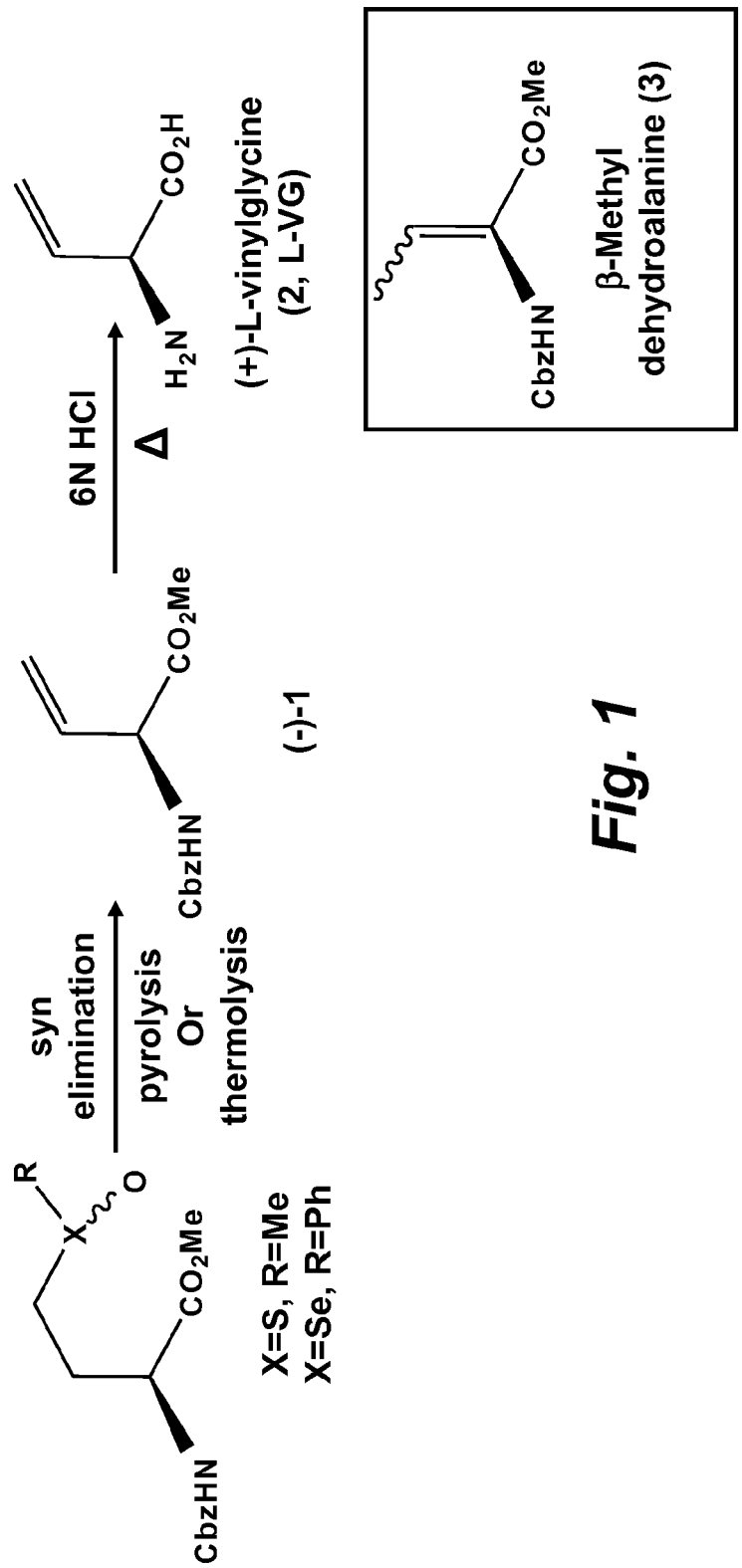
FIG. 1 is a schematic showing the conversion of protected methionine sulfoxide or aryl selenoxides to vinylglycine by conventional pyrolysis or thermolysis.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

In describing and claiming the disclosed subject matter, the following terminology will be used in accordance with the definitions set forth below.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Abbreviations

ONP: ortho-nitrophenol; PhMe, toluene;

DEFINITIONS

The term "non-polar aprotic solvent" as used herein refers to those solvents with a dielectric constant of less than about 15 are generally considered nonpolar. Such solvents do not have a permanent electric dipole moment and therefore have no tendency for intramolecular association with polar species, and are not miscible with water. Examples of such solvents include, but are not limited to, hexane, benzene, toluene, diethyl ether, dioxane, chloroform, and ethyl acetate The term "aryl" as used herein refers, unless otherwise stated, to a polyunsaturated, typically aromatic, hydrocarbon substituent which can be a single ring or multiple rings (up to three rings) which are fused together or linked covalently. The term "heteroaryl" as used herein refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include, but are not limited to, phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl, 4-pyridazinyl, 5-benzothiazolyl, purinyl, 2-benzimidazolyl, 5-indolyl, 1H-indazole, carbazole, β-carboline, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl and 8-quinolyl.

The term "aryl" as used herein can refer to a phenyl or naphthyl group which is unsubstituted or substituted. The term "heteroaryl" may refer to a pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, isoquinolyl, quinoxalinyl, quinoxalinyl, quinolyl or quinolyl group which is unsubstituted or substituted.

The term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "aryl" and "heteroaryl") is meant to include both substituted and unsubstituted forms of the indicated radical, unless otherwise indicated Similarly, substituents for the aryl and heteroaryl groups are varied and can be selected from, but not limited to, such as: -halogen, —OR, —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$).dbd.NH, —NR'C(NH$_2$)=NH, —NH—C(NH$_2$).=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_2$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_2$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

The term "alkyl" as used herein refers to saturated monovalent hydrocarbon groups having straight, branched, or cyclic moieties (including fused and bridged bicyclic and spirocyclic moieties), or a combination of the foregoing moieties. For an alkyl group to have cyclic moieties, the group must have at least three carbon atoms.

The term "protecting group" refers to any chemical moiety that may be attached to a compound, including an intermediary compound in a reaction, thereby preventing undesirable modification of the structure to which the protecting group is attached. Their introduction and removal are described, for example, in "Protective Groups in Organic Synthesis", T. W. Greene et al., John Wiley & Sons Inc., Second Edition 1991. Suitable protecting group donor compounds, e.g. amino group protecting agents, are well-known to a skilled person and may include, but are not limited to, anhydrides, halides, carbamates or N-hydroxysuccinimides, carboxybenyl, and methoxy (MeO). It will be recognized that it may be preferred or necessary to prepare such a compound in which a functional group is protected using a conventional protecting group, then to remove the protecting group, to provide a compound of the present disclosure. The details concerning the use of protecting groups in accordance with the present invention are known to those skilled in the art.

The term "amino-protecting group" as used herein refers to a protecting group that preserves a reactive amino group that otherwise would be modified by certain chemical reactions. Non-limiting examples of amino protecting groups include the formyl group or lower alkanoyl groups with 2 to 4 carbon atoms, in particular the acetyl or propionyl group, the trityl or substituted trityl groups, such as the monomethoxytrityl group, dimethoxytrityl groups such as the 4,4'-dimethoxytrityl or 4,4'-dimethoxytriphenylmethyl group, the trifluoroacetyl, and the N-(9-fluorenyl-methoxycarbonyl) or "FMOC" group, the allyloxycarbonyl group or other protecting groups derived from halocarbonates such as (C$_6$-C$_{12}$) aryl lower alkyl carbonates (such as the N-benzyloxycarbonyl group derived from benzylchlorocarbonate), such as the benzyloxycarbonyl (CBZ group), or derived from biphenylalkyl halo carbonates, or tertiary alkyl halo carbonates, such as tertiary-butylhalocarbonates, in particular tertiary butylchlorocarbonate, or di(lower)alkyldicarbonates, in particular di(t-butyl)-dicarbonate, and the phthalyl group.

The term "amino acid" as used herein refers to any amino acid or derivative thereof that may be incorporated into a peptide via a peptide bond, including, but not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

DESCRIPTION

The present disclosure encompasses methods for the mild thermolysis of sulfoxides to generate alkenes. The present disclosure further provides methods that encompass approaches to synthesize (S)-homocysteine (homocysteine) sulfides and sulfoxides (homocysteineO); (ii) a route to prepare protected L-vinylglycine esters by thermolysis; and (iii) syn-elimination efficacy of S-alkyl- and S-aryl-substituted homocysteineO esters leading to the discovery of an aryl homocysteineO capable of eliminating without isomerization under mild reflux. The present disclosure encompasses methods for generating vinylglycine under mild thermolytic conditions that can provide conversion of the precursor compound homocysteineO(o-NO$_2$Ph) to vinylglycine without isomerization, or the need to chromatographically purify the final product.

The methods of the disclosure provide an alternative to the more traditional pathways as shown, for example, in FIG. 1. By selectively blocking the amino and carboxy groups of the derivatized amino acid, the methods of the disclosure provide for the synthesis of a peptide having the vinylglycine moiety at either the carboxy or the amino terminus of the peptide. The mild conditions for the thermolytic removal of the o-NO$_2$-phenyl substituted aryl group ensure that there is minimal if any damage to thermally sensitive conjugates such as a peptide bearing the vinylglycine.

Figure 2:
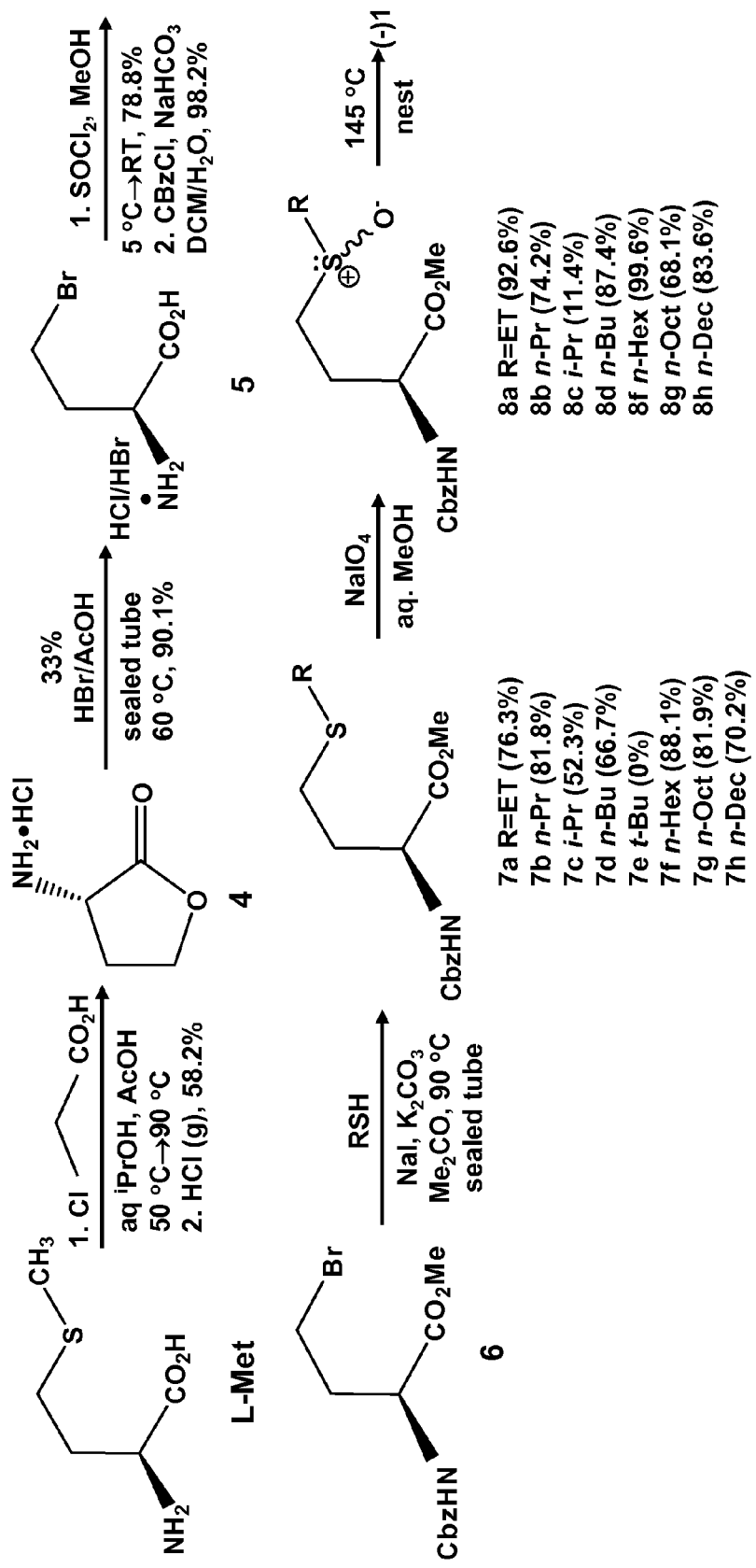
FIG. 2 is a schematic showing the synthesis of protected methionine sulfoxides with different alkyl chains from methionine via the intermediary protected (S)-bromoethylglycine 6.

Comparisons of Thermolysis of Methionine Sulfoxide Alkyl Analogs (a) Synthesis of Methionine Sulfoxide Alkyl Analogs The methods of the disclosure provide a route to sulfoxides through the thiolation and subsequent oxidation of protected (S)-bromoethylglycine 6 that may be prepared from L-methionine, as shown in Scheme 2, FIG. 2. The unprotected bromoethylglycine 5 was obtained in 2 steps, beginning with the lactonization of an S-alkylated L-methionine sulfonium salt generated in situ with chloroacetic acid. Subsequent acid catalyzed intramolecular displacement of the dialkylsulfide provided (S)-homoserine lactone HCl (4) in about a 60% yield. Treatment of the lactone with 33% hydrobromic acid/acetic acid followed by N,O protection of the mixed bromide salt 5 with carboxybenzene and methyl groups then provided (S)-bromoethylglycine 6.

The homocysteine(homocysteine)(alkyl)esters 7a-7g (shown in FIG. 2) were then prepared by nucleophilic thiolation of the (S)-bromoethylglycine 6 under Finkelstein conditions (Finkelstein H. (1910) *Ber.,* 43: 1528, incorporated herein by reference in its entirety). Reactions were performed in a sealed tube to avoid volatile thiol evaporation. The alkyl sulfides 7a-7g were obtained in about 50 to about 90% yield with the exception of protected homocysteine(tert-butyl) 7e that failed to form by this method. Oxidation of the various sulfides 7a-7g by aqueous sodium periodate then provided the corresponding homocysteineO(alkyl) esters 8a-8g (shown in FIG. 2) as a mixture of diastereomers.

(b) Thermolysis of Methionine Sulfoxide Alkyl Analogs

The thermolysis experiments were conducted on each sulfoxide 8a-8g on a 0.1 mmol scale at 145° C. with agitation over a 3 day period. $^1$H NMRs were taken daily to monitor the progress of the solventless reactions, and to provide ratio estimates of (S)-Cbz-vinylglycine-OMe (1), α,β-unsaturated isomer (3), and the starting materials (8a-8g) (as shown in FIG. 2, Scheme 2). The syn-elimination rate for Cbz-MetO—OMe was found to be appreciably less than for the multi-carbon chain analogs, as shown in column 3, Table 1.

TABLE 1

Syn elimination results of homocysteineO(alkyl) esters 8a-8g

| R= | ° C. | Time (h) | mm Hg | Ratio of Final Products 1:3:8[a] | yield, %[b] |
|---|---|---|---|---|---|
| Me | 145 | 72 | 760 | 0.3:0:1 | 12.3c |
| Me | 190 | 2 | 760 | 1:0.7:0.7 | 1.2c |
| Et (8a) | 145 | 72 | 760 | 0.8:0.3:1 | — |
| n-Pro (8b) | 145 | 42 | 760 | 0.6:0.1:1 | — |
| n-Pro (8b) | 145 | 72 | 760 | 0.5:0.4:1 | 47.1 |
| i-Pro (8c) | 145 | 72 | 760 | 0.2:0:1 | — |
| n-But (8d) | 145 | 42 | 760 | 0.8:0.1:1 | — |
| n-But (8d) | 145 | 72 | 760 | 0.7:0.3:1 | 49.8 |
| n-But (8d) | 190 | 5 | 3 | 1:0:0.2 | 30.3 |
| n-Hex (8e) | 145 | 72 | 760 | 1:0:0.8 | 35.1 |
| n-Oct (8f) | 145 | 72 | 760 | 1:0.1:0.7 | 18.2 |
| n-Dec (8g) | 145 | 72 | 760 | 1:0.1:1.4 | 41.3 |

[a]Estimate based on integrations in crude 1H NMR (vinylglycine 1:α,β-isomer 3:oxygenated Cbz-MetO—OMe(aryl) 8)
[b]Isolated yield
[c]Contained α,β-unsaturated isomer 3

No isomerization was observed at 145° C. However, a large amount of unconverted MetO ester remained after 72 h. Following purification on silica, the isolated vinylglycine product was contaminated with α,β-isomer 3 suggesting that migration of the double bond occurred during chromatography. This was supported when pure Cbz-vinylglycine-OMe (−)-1 was stirred in a hexanes:ethyl acetate (3:1) slurry of silica gel at room temperature. Subsequent NMR analysis revealed that one-third of the sample converted to the α,β-unsaturated ester, thereby providing evidence that SiO$_2$ is capable of catalyzing the isomerization during purification reducing yields.

The thermolysis studies conducted on the seven alkyl chain analogs (8a-8g, FIG. 2) revealed that the elimination rate could yield higher amounts of pure (S)-Cbz-vinylglycine-OMe 1 after 72 h. HomocysteineO(n-Bu) ester 8d provided the highest yield of those tested. A common theme among all the alkyl sulfoxides evaluated was the slow elimination rate. However, the prolonged exposure to heat appeared to increase isomer formation, presumably from the vinylglycine ester 1, and that the duration of the thermolysis needed to be substantially reduced to optimize the reaction.

Figure 3:
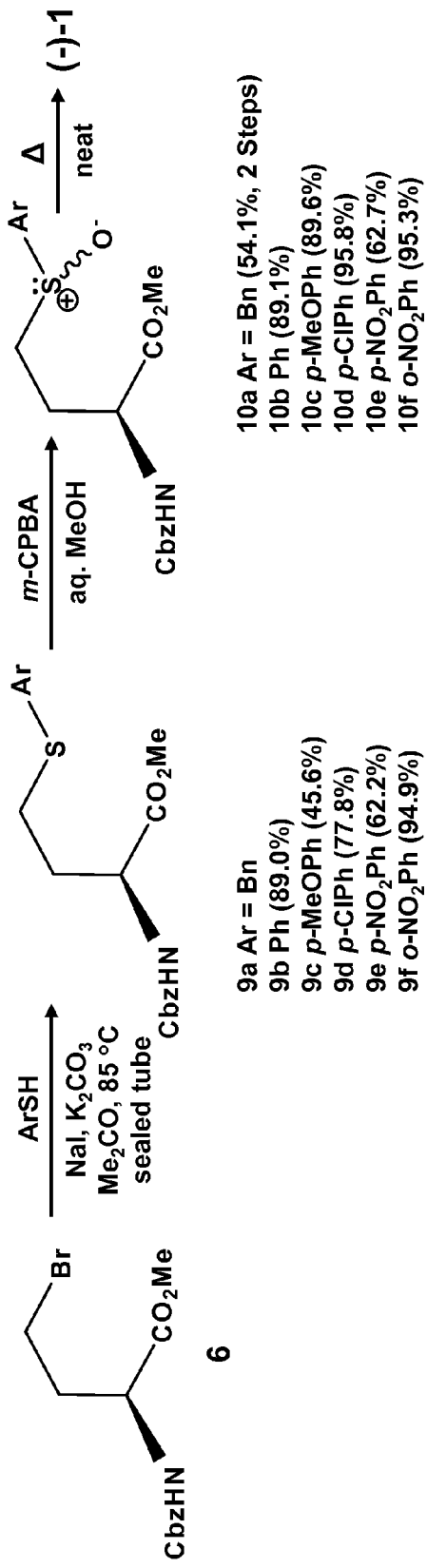
FIG. 3 is a schematic of the synthesis of aryl-containing sulfoxide analogs from (S)-bromoethylglycine 6.

Comparisons of Thermolysis of Methionine Sulfoxide Aryl Analogs (a) Synthesis of Methionine Sulfoxide Aryl Analogs The elimination reaction of aryl-containing sulfoxides (10a-10f, as shown in FIG. 3) was examined. The (S)-homocysteine(aryl) analogs compared were prepared from (S)-bromoethylglycine 6 in the same manner as described above for the alkyl variants, followed by oxidation with m-CPBA, which afforded higher yields than did sodium periodate (as schematically shown in FIG. 3). Synthesis of homocysteineO (o-NO$_2$Ph) 10f first required the preparation of o-nitrothiophenol 11 via Ph$_3$P-mediated reduction of its commercially disulfide, as shown schematically in FIG. 4.

(b) Thermolysis of Methionine Sulfoxide Aryl Analogs

The solventless thermolytic studies, the results of which are shown in Table 2, were monitored by $^1$H NMR. The elimination rates for aryl sulfoxides were found to be greater than their homocysteineO(alkyl) counterparts. Referring, for example, to FIG. 3. initially evaluated was homocysteineO (Ph) 10b that decomposed after 18 h to the desired olefin 1, a trace amount of the α,β-isomer 3 and unexpectedly, some deoxygenated homocysteine(Ph) 9b. Chromatography purification on silica however yielded only 54.1% of pure (S)-Cbz-vinylglycine-OMe (−)-1.

Additional reactions were performed on homocysteineO (Ph) 10b to screen alternative conditions, and all were found to increase reduced side product 8b formation including: low pressure (3 mmHg); reflux in dimethylformamide; and higher temperature (190° C./0.15 h). At temperatures of less than 140° C., the elimination rate diminished and the deoxygenated side product increased proportionally with longer durations of heat exposure.

Results comparable to those obtained from the thermolysis of homocysteineO(Ph) 10b (aboe) were observed for substituted phenyl analogs with the exception of homocysteineO (p-MeOPh) 10c that appeared to have the greatest susceptibility to side product formation (Table 2). This was, however, not unexpected as the pyrolysis of substituted aryl sulfoxides deduced a correlation between syn-elimination rate and phenyl ring substituents. Thus, Emerson & Korniski *J. Org. Chem.* (1969), 34: 4115 established that para-situated electron-donating groups (for example, methoxy or methyl substituents) slowed the pyrolysis of aryl n-propyl sulfoxides while electron-releasing moieties (for example, halogens such as Cl, Br and the like, $NO_2$, $SO_2$ and the like) enhanced the rate.

The substitution effect was seen for the homocysteineO (Ar) variants 10c-10f with homocysteineO(p-MeOPh) 10c as the only aryl analog with unconverted sulfoxide remaining after 18 h. The thermolysis of homocysteineO(p-ClPh) and homocysteineO(p-$NO_2$Ph), esters 10d and 10e respectively, were complete within this period with only traces of isomer present. It was also determined with these analogs that the time of thermolysis could be reduced to 15 min by applying a temperature of 190° C. with limited side product formation.

TABLE 2

Thermolytic syn elimination results of homocysteineO(aryl) esters 10a-10g

| R= | ° C. | Time (h) | mm Hg | Ratio of Final products 1:9:10[a] | yield, %[b] |
|---|---|---|---|---|---|
| Bn (10a) | 145 | 72 | 760 | 0:6.0:1[c] | 29.9 |
| Bn (10a) | 145 | 10 | 3 | 0.1:0:1 | — |
| Ph (10b) | 145 | 18 | 760 | 1:0.1:0 | 54.1 |
| Ph (10b) | 145 | 10 | 3 | 1:0.3:0.3 | 57.9 |
| Ph (10b) | 190 | 0.15 | 760 | 1:0:0.3[c] | 25.0 |
| p-MeOPh (10c) | 145 | 18 | 760 | 1:0.4:0.2 | 35.5 |
| p-MeOPh (10c) | 190 | 0.15 | 760 | 1:0.4:0.2[c] | 9.2 |
| p-ClPh (10d) | 145 | 18 | 760 | 1:0:0[c] | 41.0 |
| p-ClPh (10d) | 190 | 0.15 | 760 | 1:0.1:0[c] | 67.0 |
| p-$NO_2$Ph (10e) | 145 | 19 | 760 | 1:0:0[c] | 53.9 |
| p-$NO_2$Ph (10e) | 190 | 0.15 | 760 | 1:0:0 | 62.9 |
| o-$NO_2$Ph (10f) | 145 | 0.15 | 760 | 1:0:1.3 | — |
| o-$NO_2$Ph (10f) | 145 | 1 | 760 | 1:0:0 | 35.5 |
| o-$NO_2$Ph (10f) | 100 | 18 | 760 | 1:0:2.8 | — |

[a]Estimate based on relative $^1$H peak areas in crude NMR (vinylglycine 1:deoxygenated homocysteine(aryl) 9:oxygenated homocysteine(aryl) 10)
[b]Isolated yield
[c]C Contained α,β-unsaturated isomer 3

Thermolytic Production of Vinylglycine from homocysteineO(o-nitrothiophenol sulfoxide) (10f)

Electron-withdrawing group influence on syn-elimination was examined for aryl selenoxides, and it was found that a nitro group ortho positioned substantially accelerated the reaction, causing decomposition to o-nitrophenyl selenol and 1-dodecene at 25° C. (Sharpless & Young (1975) *J. Org. Chem.* 40: 947). The thermolysis rate, therefore, of homocysteineO(o-$NO_2$Ph) 10f was also tested.

Upon heating at 145° C., decomposition of the homocysteineO(o-nitrothiophenol sulfoxide) 10f was observed within minutes, and after 1 h the thermolysis was complete. NMR analysis of the crude product revealed 100% conversion to the desired the vinylglycine ester and the absence of both isomer and deoxygenated side products, as shown in Table 2. The crude material was chromatographed on silica to provide pure Cbz-vinylglycine-OMe with about a 35% yield. Temperatures as low as about 100° C. were found also to be capable of catalyzing the thermolysis of the o-nitrophenyl sulfoxide 10f.

Figure 5:
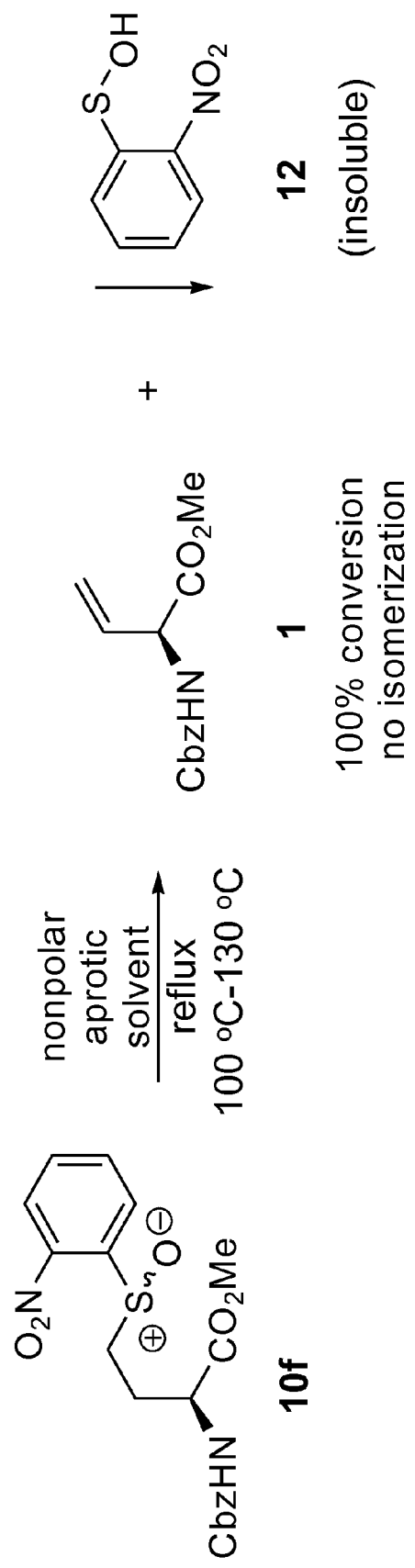
FIG. 5 is a schematic showing the thermolysis of (s)-homocysteine(o-nitrophenyl sulfoxide) 12 in the presence of a nonpolar, aprotic solvent and mild temperature to yield protected vinylglycine 1.

Of solvents screened for the reaction, including dichloromethane, chloroform, and benzene, higher boiling (100° C.-130° C.) nonpolar, aprotic solvents such as dioxane were found to effect the transformation. Toluene, however, caused unwanted side product formation. An addition advantage of the methods of the disclosure (as schematically shown in FIG. 5) is that the precipitated sulfenic acid 12 byproduct was water-soluble and could be removed by filtration.

These methods of the present disclosure, therefore, encompass the use of 2-nitrophenylsulfoxide as an effective alternative to aryl selenides for the production of vinylglycine under mild reflux conditions. The reactions of the disclosure do not cause isomerization. Furthermore, the ability to obtain pure protected vinylglycine by non-chromatographic means is advantageous.

The methods of the disclosure, by generating the vinylogous substituent under mild reflux, enable the incorporation of vinylglycine into molecules that would otherwise be sensitive to pyrolysis or oxidation. The 2-nitrophenyl sulfoxide derivative of homocysteine is stable to acids such as, but not limited to, acetic acid, trifluoroacetic acid, HCl, and the like, and therefore provides a means to build peptides from either the N or C terminus by selecting the appropriate removable protecting groups such as tert-butyloxycarbonyl and Me, respectively. Incorporation of the 2-nitrophenyl group is also offers an advantage in that the intense yellow bands of compounds incorporating this group may be readily visualized during silica chromatography, and the compounds may be easily detected as they elute from the column.

Figure 6:
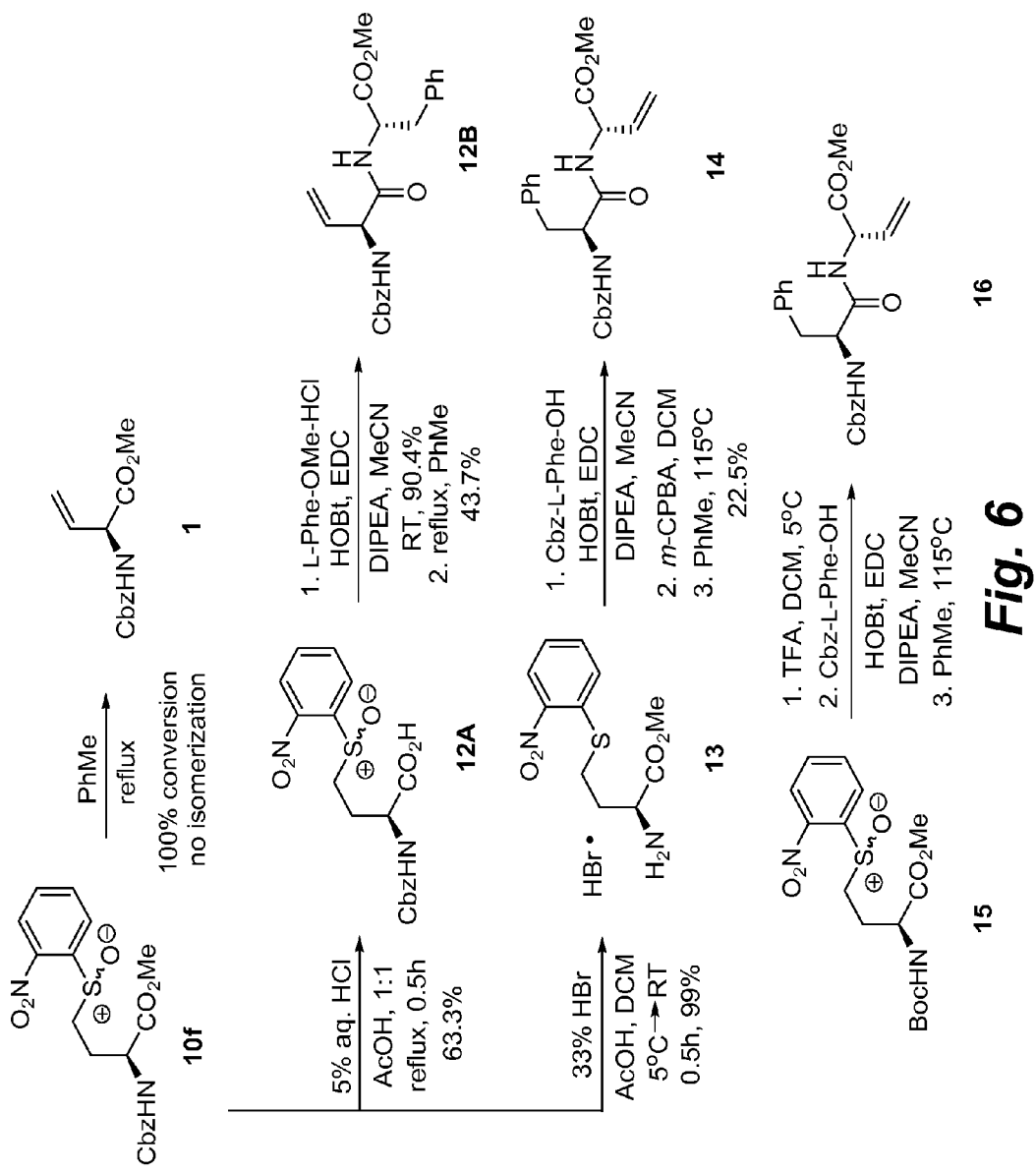
FIG. 6 is a schematic showing the synthesis of vinylglycine-phenylalanine.

As shown in FIG. 6, and as described in Examples 38-41, below, are reactions for the synthesis of a vinylglycine-phenylalanine dipeptide (with protecting groups attached in compounds 12b, 14 and 16).

General Alkene Synthesis o-Nitrophenyl sulfoxides have been found to be efficient synthetic precursors of various alkene types. Under toluene reflux over sodium acetate, substituted and terminal alkenes were generated in high purity upon precipitation of the o-nitrophenyl sulfenic acid byproduct removable by simple filtration. The methods of the present disclosure have practical applications for the preparation of unsaturated compounds under mild, thermolytic conditions.

A commonly used method to introduce double bonds into molecules is through thermal β-eliminations. Although a range of precursors (i.e. amine oxides (Cope et al., (1949) *J. Am. Chem. Soc.*, 71: 3929-3925); DePuy & King (1960) *Chem. Rev.* 60: 431-457); quarternary ammonium iodides (Hofmann, A. W. (1881) *Ber. Dtsch. Chem. Ges.*, 14: 494-496; Hofmann, A. W. (1881) *Ber. Dtsch. Chem. Ges.*, 14: 659-669; Cope & Trumbell (1960) *Org. React.* 11: 317-493); tosylhydrazones (Bamford & Stevens (1952) *J. Chem. Soc.* 4735-4750; Shapiro, R. H. (1976) *Org. React.* 23: 405-507; Adlington & Barrett (1983) *Acc. Chem. Res.* 16: 55-59); xanthate esters (Chugaev, L. (1899) *Ber. Dtsch. Chem. Ges.* 32: 3332-3335; Nace, H. R. (1962) *Org. React.* 12: 57-100); Sharpless & Young (1975) *J. Org. Chem.* 40: 947-949); sulfoxides (Field, L. (1972) *Synthesis* 101-133; Trost et al., (1976) *J. Am. Chem. Soc.* 98: 4887-4902; Trost, B. M. (1978) *Chem. Rev.* 78: 363-382); selenoxides (Grieco et al., (1976) *J. Org. Chem.* 41: 1485-1486) may be employed, the reaction can have limited utility for compounds sensitive to harsh temperatures or bases. The efficacies of homocysteine sulfoxides conversion to vinylglycines has now been shown, and it has been discovered that the o-nitrophenyl (ONP) analog underwent synperiplanar β-elimination at temperatures as low as 100° C., allowing for the application of ONP-sulfoxides for generating alkenes under mild, thermolytic conditions.

Figure 8:
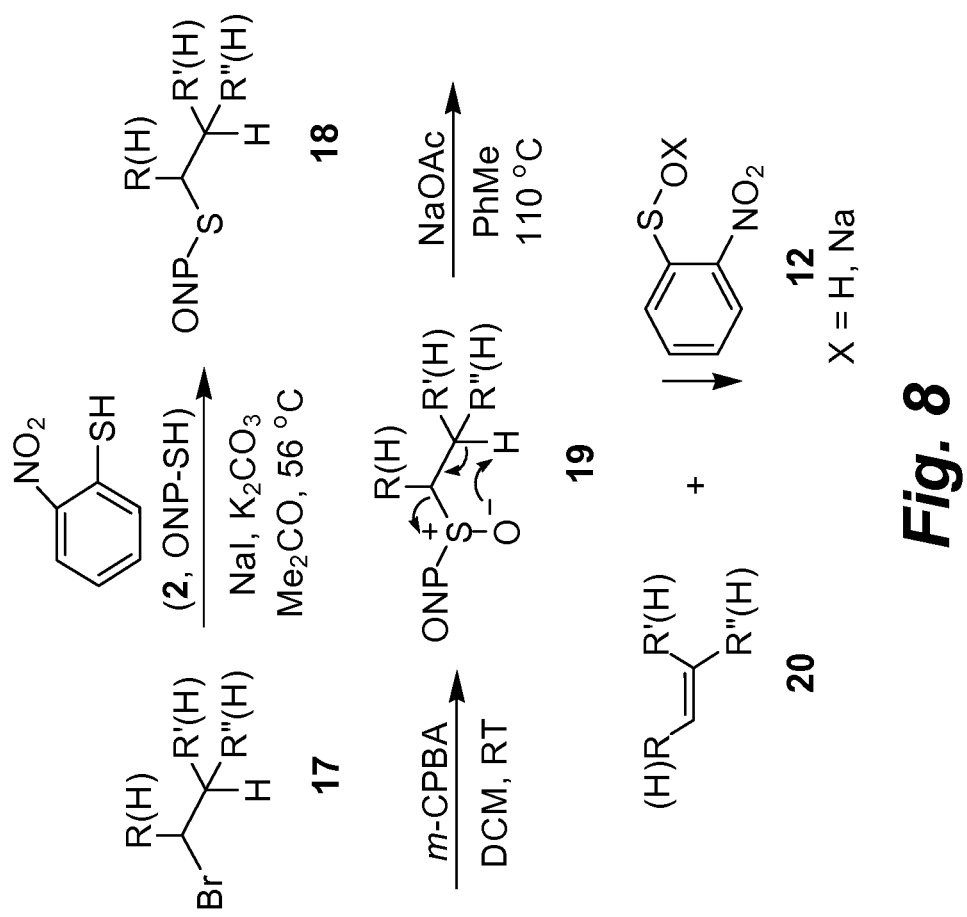
FIG. 8 is a schematic illustrating the synthesis of alkenes from alkyl halides via o-nitrophenyl sulfoxides 19 by thermal β-elimination.

Exemplary ONP-sulfoxides (19) used for the study were synthesized from alkyl halides and 2-nitrothiophenol under alkaline Finkelstein conditions (Finkelstein, H. (1910) *Ber. Dtsch. Chem. Ges.* 43: 1528-1532) by the general route schematically depicted in FIG. 8. Subsequent oxidation of sulfides 18 with m-CPBA afforded sulfoxides 19 in good overall yields. The elimination reactions were then performed under toluene reflux with an inorganic base to neutralize the ONP sulfenic acid 12 byproduct. Although not required, the base supplement prevented decomposition of the acid into toluene-soluble impurities, thereby yielding the alkenes in high purity. Potassium and sodium carbonates, and sodium bicarbonate were all found to be effective in the neutralization; however, sodium acetate was preferred as it did not induce isomerization of the double bond in sensitive molecules.

Figure 9:
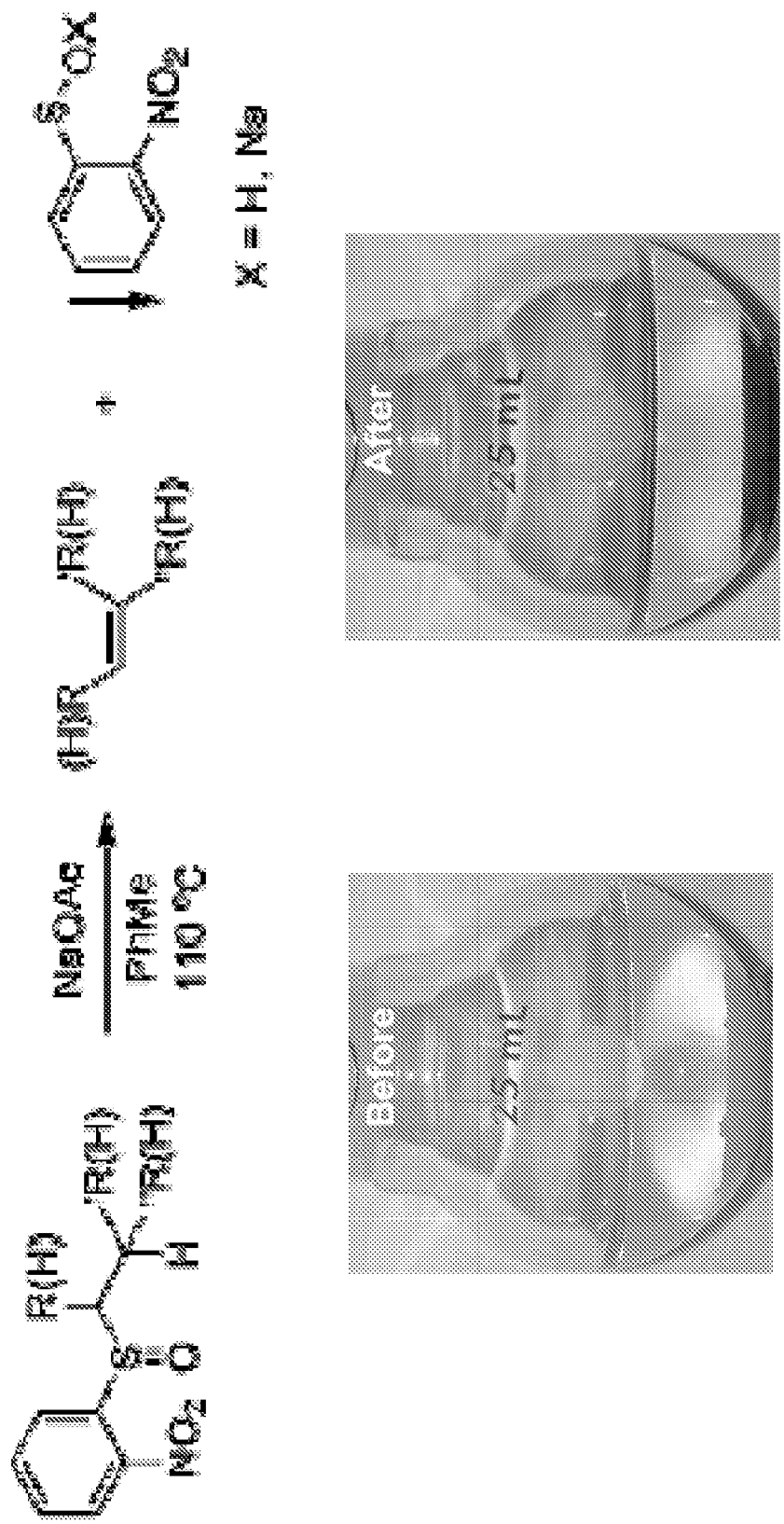
FIG. 9 is a schematic illustrating the preparation of terminal and substituted alkenes from o-nitrophenyl sulfoxides.
Figure 10:
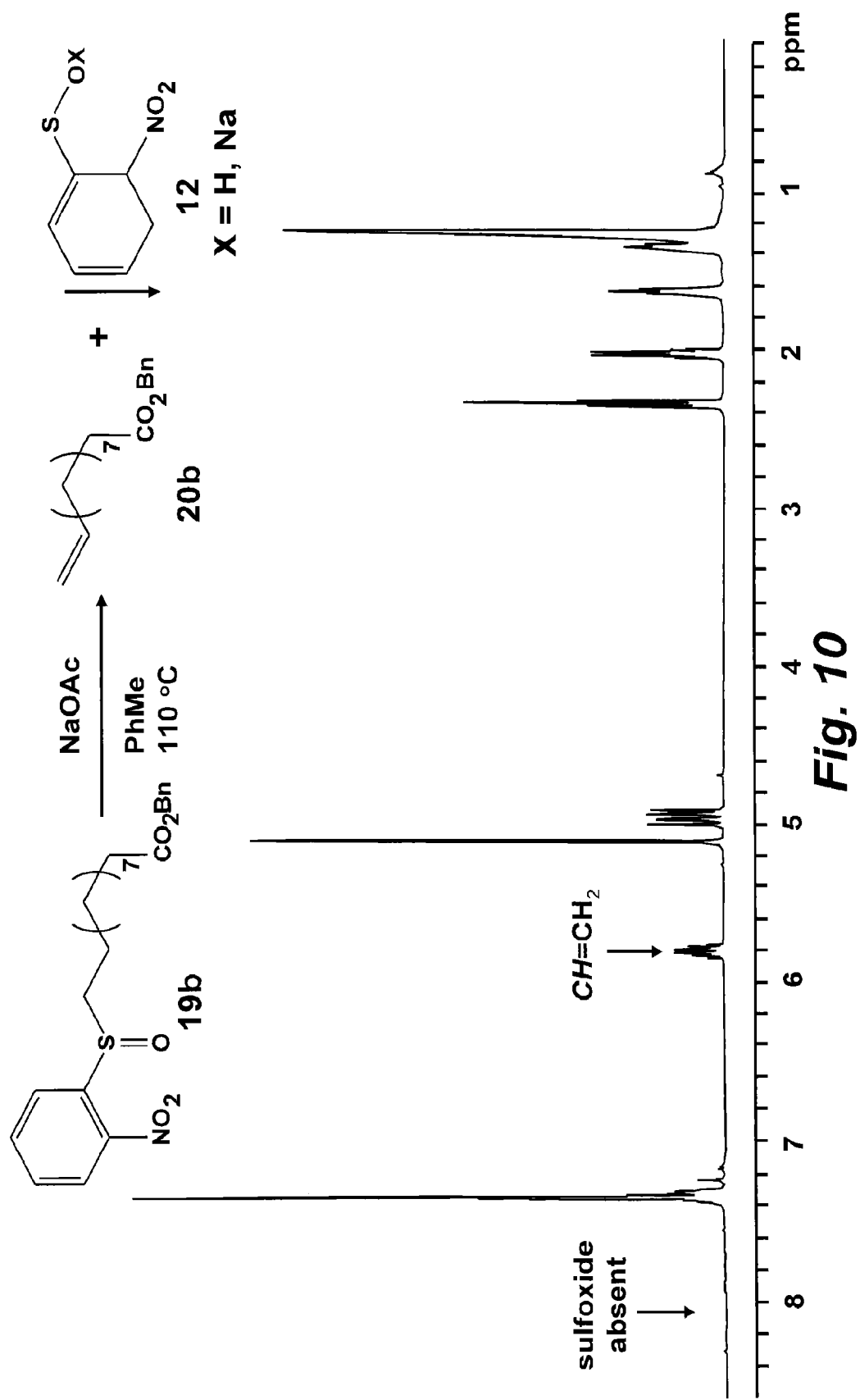
FIG. 10 is an image of an NMR output of the filtered reaction product 20b prior to chromatographic purification.

Upon reflux over sodium acetate, the toluene solutions of the sulfoxides faded slowly from bright yellow due to precipitation of sulfenic acid 12, as shown in FIG. 9. As thermolysis of this byproduct continued, the solvent turned pale or colorless and the solid sodium acetate darkened by the acid being absorbed. After the reactions were complete, the salt impurities were removed by simple vacuum filtration through Celite. Concentration of the filtrate yielded the alkenes in high purity, as illustrated by the crude $^1$H NMR of ester 20b shown in FIG. 10.

Figure 11:
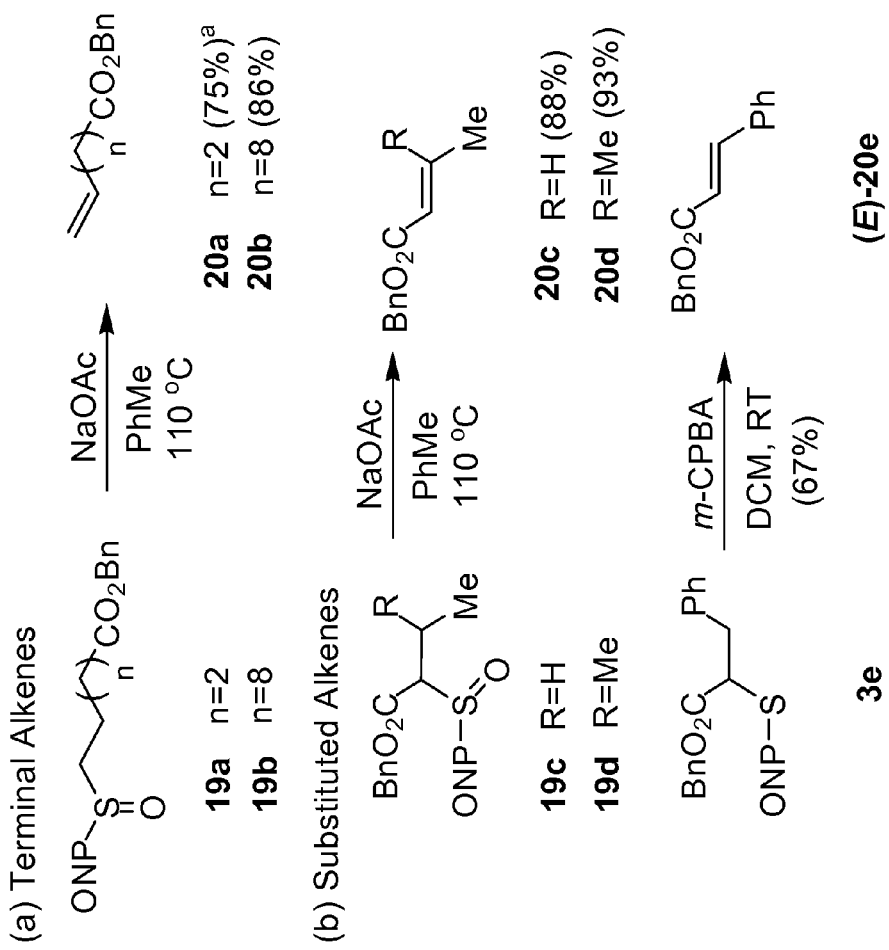
FIG. 11 is a schematic illustrating the preparation of terminal and substituted alkenes.

The practical use of ONP-sulfoxides in synthesizing terminal alkenes was evaluated, as shown in FIG. 11 (part (a)). Under the thermolytic conditions described, alkenes 20a and 20b were successfully generated with no detectable side products such as deoxygenated sulfoxide and isomerized alkene.

Obtained likewise in high yield and purity were substituted alkenes 20c and 20d, shown in FIG. 11 (part (b)), demonstrating the ONP-sulfoxides as capable precursors of α,β-unsaturated esters in hindered substrates. In the case of sulfoxide 19c, only the trans product 20c was observed and, surprisingly, a trace amount of the alkene was isolated during the preceding S-oxidation reaction. While not wishing to be bound by any one theory, this suggested that certain ONP-sulfoxides could syn eliminate without heat catalysis contingent on the pKa of the β-hydrogen atom. Phenyl was shortly after identified as a group that conferred the acidity needed to prompt expulsion of acid 12 during oxidation of sulfide 3e and providing (E)-benzyl cinnamate (20e) in situ at room temperature. In addition, aqueous work up with 5% sodium bicarbonate was found to cause partial or complete elimination in sulfoxides with sufficient β-proton acidities.

Figure 12:
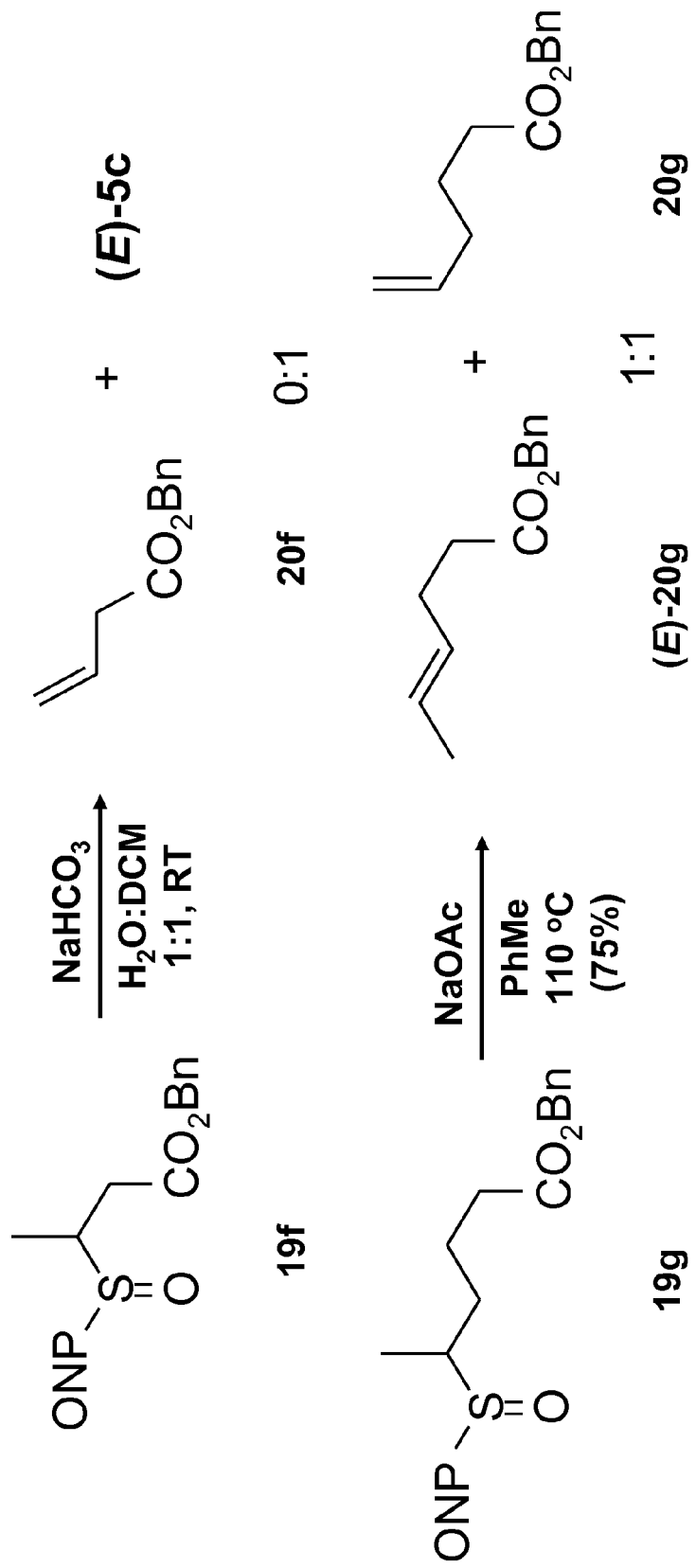
FIG. 12 is a schematic illustrating the terminal vs. substituted alkene generation.

Correspondingly, the eliminations were effected in the absence of heat for esters positioned β to the ONP-sulfoxide. The quantitative conversion of ester 19f was observed within minutes under reflux and when performed at room temperature using basic biphasic conditions, the α,β-unsaturated ester (E)-20c was the only product isolated from the organic layer (see FIG. 12). The relevance of β-hydrogen acidities was further probed by evaluating directional preferences in ONP-sulfoxide 19g that possessed negligible differences in the pKa's. The reaction afforded a 1:1 mixture of alkenes 20a and 20g, thus revealing a lack of influence in the degree of carbon substitution and the significance of β-proton acidity on product outcome.

Figure 13:
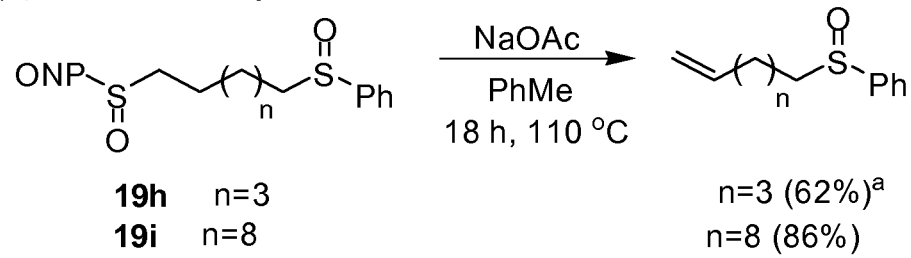
FIG. 13 is a series of reaction schematics comparing o-nitrophenyl sulfoxide efficacy with reported aryl sulfoxides. Reaction (a)—Field, L. (1972) *Synthesis* 101-133; Trost et al., (1976) *J. Am. Chem. Soc.* 98: 4887-4902; Trost, B. M. (1978) *Chem. Rev.* 78: 363-382); Emerson & Korniski (1969) *J. Org. Chem.* 34; 4115-4118; Trost & Kunz (1974) *J. Org. Chem.* 39: 2648-2650; Koppel & Kinnick (1975) *Chem. Commun.* 12: 473; Tanikaga et al., (1977) *Synthesis* 5: 299-301; Zonjee et al., (1989) *Tetrahedron* 45: 7553-7564; Moghaddam & Ghaffarzadeh (1996) *Tetrahedron Lett.* 37: 1855-1858; Reaction (b)—Emerson & Korniski (1969) *J. Org. Chem.* 34; 4115-4118; Cinquini et al., (1985) *Gazz. Chim. Ital.* 115: 347-350; Reaction (c)—Emerson & Korniski (1969) *J. Org. Chem.* 34; 4115-4118; Ishibashi et al., (1985) *Tetrahedron Lett.* 26: 5791-5794; Ishibashi et al., (1987) *Chem. Res., Synop.* 9: 296-297; and Reaction (d)—Emerson & Korniski (1969) *J. Org. Chem.* 34; 4115-4118.
Figure 13:
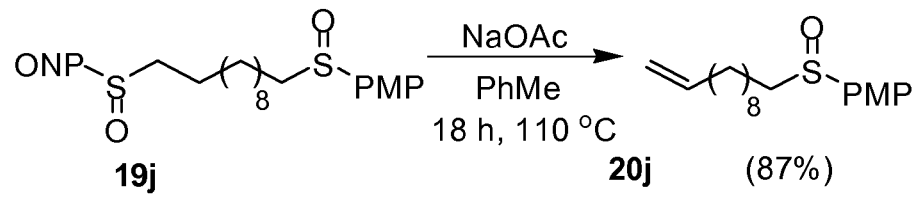
Figure 13:
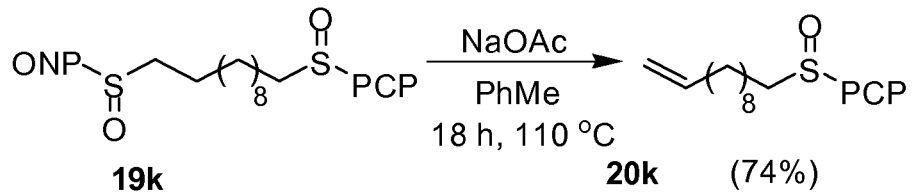
Figure 13:
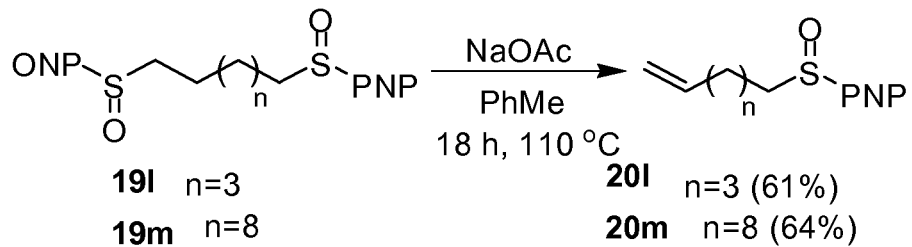

The relative efficiency of ONP-sulfoxide eliminations was evaluated in direct comparison with reported aryl sulfoxides (Field, L. (1972) *Synthesis* 101-133; Trost et al., (1976) *Am. Chem. Soc.* 98: 4887-4902; Trost, B. M. (1978) *Chem. Rev.* 78: 363-382; Emerson & Korniski (1969) *J. Org. Chem.* 34: 4115-4118; Trost & Kunz (1974) *J. Org. Chem.* 39: 2648-2650; Koppel & Kinnick 91975) *Chem. Commun.* 12: 473; Tanikaga et al., (1977) *Synthesis* 5: 299-301; Zonjee et al., (1989) *Tetrahedron* 45: 7553-7564; Moghaddam & Ghaffarzadeh (1996) *Tetrahedron Lett.* 37: 1855-1858; Cinquini et al., (1985) *Gazz. Chim. Ital.* 115: 347-350; Ishibashi et al., (1985) *Tetrahedron Lett.* 26: 5791-5794; Ishibashi et al., (1987) *Chem. Res., Synop.* 9: 296-297; Fujisawa et al., (1988) *Bull. Chem. Soc. Jpn.* 61: 1273-1279) as shown in FIG. 13. The study was performed by screening disulfoxides 19h-19m under the mild thermolysis conditions established for the ONP-sulfoxides. Phenyl sulfoxides which are often used to prepare alkenes (Field, L. (1972) *Synthesis* 101-133; Trost et al., (1976) *Am. Chem. Soc.* 98: 4887-4902; Trost, B. M. (1978) *Chem. Rev.* 78: 363-382; Emerson & Korniski (1969) *J. Org. Chem.* 34: 4115-4118; Trost & Kunz (1974) *J. Org. Chem.* 39: 2648-2650; Koppel & Kinnick 91975) *Chem. Commun.* 12: 473; Tanikaga et al., (1977) *Synthesis* 5: 299-301; Zonjee et al., (1989) *Tetrahedron* 45: 7553-7564; Moghaddam & Ghaffarzadeh (1996) *Tetrahedron Lett.* 37: 1855-1858) was found to be an ineffective substrate in compounds 19h and 19i as only ONP eliminated products 20h and 20i were generated after 18 hours of reflux. This was not unexpected, as temperatures ≥140° C. or use of strong base (i.e. tert-BuOK) are typically needed to catalyze phenyl sulfoxide eliminations. p-Tolyl and p-chlorophenyl sulfoxides 20j and 20k, respectively, were similarly obtained in high yield (see FIG. 13) thereby demonstrating that harsher conditions are also required to prompt their reaction.

A comparison was also performed to establish the effect of nitro group positioning, as shown in FIG. 13 (part (d)). It was found that with p-nitrophenyl sulfoxides that partial thermolysis under toluene reflux can occur. Although a minor amount of bis-eliminated alkene was generated during the reaction, the absence of ONP-sulfoxide in the crude product indicated that the ortho position maximizes the effect of the nitro group to promote β-elimination. Such electronic influences were similarly observed by Sharpless and Young in their evaluation of aryl selenoxides (Sharpless & Young (1975) *J. Org. Chem.* 40: 947-949).

Accordingly, o-nitrophenyl sulfoxides can serve as effective precursors of different alkene types. Their ability to convert under mild reflux and essentially neutral conditions makes them useful substrates for generating unsaturation in molecules. As noted, β-eliminations typically require harsh conditions that may include strong bases and prolong heating at 140° C. or above. Phenyl selenides are often utilized in place as alkene precursors with thermal or base sensitive molecules; however, the higher cost and the toxicity associated with selenoxide use may limit reaction scales. The readily available 2-nitrothiophenol is economic and its bright yellow sulfoxides can be easily visualized on silica gel allowing for their simple purification. Likewise, the ONP chromophore is beneficial as a colorimetric indicator providing an efficient means to conduct and monitor elimination reactions.

One aspect of the present disclosure, therefore, encompasses methods for synthesizing an alkene, comprising: (a) providing a sulfoxide having the formula I:

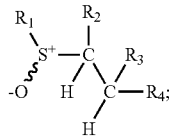

wherein: $R_1$ is an electron withdrawal group; and $R_2$, $R_3$, and $R_4$ are each independently selected from the group consisting of: H, an alkyl group, an aromatic group, an amino acid, and a peptide; (b) refluxing the compound having formula I in the presence of a non-polar and aprotic solvent, and at a temperature of about 90° C. to about 135° C., thereby generating an alkene; and (c) isolating from the non-polar aprotic solvent the alkene, wherein the alkene has the formula II:

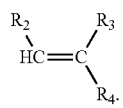

In embodiments of this aspect of the disclosure, the electron withdrawing group $R_1$ can be selected from the group consisting of: —$NO_n$, an aryl group, —RC(O)O, RC=O, XC=O, and F, wherein n is an integer from 1 to 3, and wherein X is a halogen.

In embodiments of this aspect of the disclosure, the electron withdrawing group $R_1$ may be o-nitrophenyl or p-nitrophenyl.

In some embodiments of this aspect of the disclosure, the electron withdrawing group $R_1$ can be o-nitrophenyl.

In embodiments of the methods of this aspect of the disclosure, step (b) may further comprise refluxing the compound having formula I in the presence of a base.

In these embodiments, the base can be sodium acetate.

In one embodiment of the methods of this aspect of the disclosure, $R_2$ is methyl, $R_3$ and $R_4$ are each H, and the alkene is propylene.

In another embodiment of the methods of this aspect of the disclosure, $R_2$ is a benzyl group, $R_3$ and $R_4$ are each H, and the alkene is styrene or $R_2$ is a benzyl group, $R_3$ is H, $R_4$ is a methyl group, and the alkene is β-methylstyrene.

In yet another embodiment of the methods of this aspect of the disclosure, $R_2$ is a napthyl group, $R_3$ is a phenyl group, $R_4$ is a phenyl group or a substituted phenyl, and the alkene is estrogen or a derivative thereof.

In some embodiments of the methods of this aspect of the disclosure, $R_2$ and $R_4$ are each independently selected from the group consisting of: a 2-napthyl group, a 2-anthracenyl group, and a 2-tetracenylmethyl group; and $R_3$ is H, methyl, a halide, or —OH.

Another aspect of the disclosure encompasses method for synthesizing an alkene, comprising: (a) providing a compound having formula III:

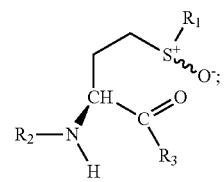

where: $R_1$ is an electron withdrawal group; $R_2$ can be selected from the group consisting of: H, a removable protecting group, an amino acid, and a peptide; $R_3$ can be selected from the group consisting of: H, a removable protecting group, an amino acid and a peptide;

and if $R_2$ is an amino acid or a peptide, $R_3$ is a removable protecting group; and if $R_3$ is an amino acid or a peptide, $R_2$ is a removable protecting group; (b) refluxing the compound having formula I in the presence of a non-polar aprotic solvent, and at a temperature of about 90° C. to about 135° C., thereby generating an alkene; and (c) isolating from the non-polar and aprotic solvent an alkene having formula VI:

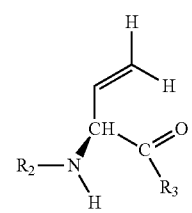

In embodiments of this aspect of the disclosure, the electron withdrawal group $R_1$ can be an aryl group selected from the group consisting of: a benzyl group, a phenyl group, a p-methoxyphenyl group, a p-chlorophenyl group, a p-nitrophenyl group, and an o-nitrophenyl group.

In one embodiment, $R_2$ is carboxybenzyl, and $R_3$ is a methoxy group

In embodiments of this aspect of the disclosure, the method may further comprise deprotecting the compound having formula II, thereby generating vinylglycine having formula V:

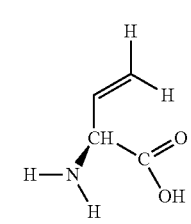

In one embodiment, $R_1$ is an o-nitrophenyl group. In another embodiment of the disclosure, $R_2$ is an amino acid, and wherein $R_3$ is a methoxy group. In these embodiments of this aspect of the disclosure, $R_2$ can be selected from, but not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In another embodiment of the disclosure, $R_2$ is a carboxybenzyl group, and wherein $R_3$ is an amino acid. In this embodiment, $R_3$ can be selected from the group consisting of:

alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In one embodiment of this aspect of the disclosure, $R_2$ is a peptide, and $R_3$ is a methoxy group.

In another embodiment of this aspect of the disclosure, $R_2$ is carboxybenzyl, and wherein $R_3$ is a peptide.

In the embodiments of this aspect of the disclosure, step (b) can further comprise including with the non-polar aprotic solvent a molar excess of sodium acetate.

In some embodiments of this aspect of the disclosure, the concentration of the sodium acetate may be from about 10 equivalents to about 50 equivalents.

In other embodiments of this aspect of the disclosure, the concentration of the sodium acetate is about 20 equivalents.

Still another aspect of the disclosure encompasses sulfoxides having the general formula I:

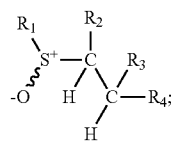

I where $R_1$ can be an electron withdrawal group; and $R_2$, $R_3$, and $R_4$ can be each independently selected from the group consisting of: H, an alkyl group, an aromatic group, an amino acid, and a peptide.

Still yet another aspect of the disclosure encompasses compounds having formula III:

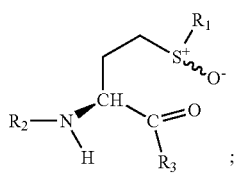

III where $R_1$ can be an aryl group selected from the group consisting of: a benzyl group, a phenyl group, a p-methoxyphenyl group, a p-chlorophenyl group, a p-nitrophenyl group, and an o-nitrophenyl group; $R_2$ is selected from the group consisting of H, carboxybenzyl, an amino acid, and a peptide; $R_3$ can be selected from the group consisting of H, MeO, an amino acid and a peptide; and if $R_2$ is an amino acid or a peptide, $R_3$ is a removable protecting group; and if $R_3$ is an amino acid or a peptide, $R_2$ is a removable protecting group.

In embodiments of this aspect of the disclosure, $R_1$ can be the aryl group o-nitrophenyl, $R_2$ can be carboxybenzyl, and $R_3$ can be a methoxy group, said compound having formula IV:

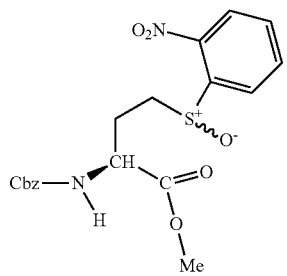

IV

In embodiments of this aspect of the disclosure, if $R_2$ or $R_3$ is an amino acid, said amino acid can be selected from, but not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

Thin layer chromatography was performed on aluminum-backed Analtech 60-$F_{254}$ silica gel plates. Sample detection was by using a 254-nm UV lamp and potassium permanganate stain for visualization. Products were purified on 60-100 mesh silica (Sorbtech, Atlanta, Ga.) or a SP1™ Purification System (Biotage, Charlottesville, Va.) equipped a $UV_{254}$ detector using KP-Sil™ cartridges (Biotage). $^1H$ and $^{13}C$ NMRs were obtained on a 500 MHz Varian Utility Plus spectrometer and referenced to residual $CDCl_3$ or $CD_3OD$. High resolution mass spectrometry (HRMS) was performed on a Bruker APEX-2 spectrometer. Specific rotation was determined on an ADP220 polarimeter (Bellingham & Stanley Ltd., Atlanta, Ga.). Melting points were obtained on a Mel- Temp (Barnstead,) and were uncorrected. 2-Nitrophenyl disulfide was purchased from Alfa Aesar and used without purification.

Example 2

(S)-3-Amino-dihydrofuran-2(3H)-one.HCl (4) Synthesis

Referring now to FIG. 2, L-Methionine (30 g, 0.201 mol) was suspended in isopropanol (100 mL), water (100 mL), and acetic acid (40 ml). Chloroacetic acid (18.9 g, 0.201 mol) was added and the solution was heated to an internal temperature of 50° C. with stirring for 2 hrs. The fully dissolved mixture was then heated for 5 hrs to an internal temperature of 90° C. that caused the solution to turn from colorless to orange. The liquid was then evaporated and the oil concentrate was heated at 90° C. for 2 hrs under reduced pressure with flask rotation on a rotary evaporator. The orange, semi-solid slurry was next suspended in anhydrous dioxane (30 mL), chilled in an ice bath, and HCl was bubbled into the solution for 2 mins. The flask was capped, removed from the ice bath, and stirred at room temperature for 3 hrs. The fine, white precipitate was then filtered, washed with ethyl acetate, and dried under vacuum. Crude lactone 4 (16.1 g, 0.117 mol) was obtained in 58.2% yield and used without further purification.

Example 3

(S)-2-Amino-4-bromobutanoic acid.HCl/HBr (5) Synthesis

Referring now to FIG. 2, in a 150 mL sealed tube was suspended lactone 4 (14.7 g, mmol) in 40 mL of about 30% hydrobromic acid/acetic acid. The container was sealed tightly and the solution stirred in a heated oil bath at 60° C. for 15 hrs. The tube was removed from the oil bath and allowed to stand at room temperature for 2 hrs. The salt was filtered, washed with ethyl acetate, and dried under vacuum. The off-white product with a m.p. of 179° C.-182° C. was obtained in 90.1% yield. $^1$H NMR (500 MHz, CD$_3$OD) δ 3.99 (t, 1H, J=6.5 Hz), 3.51-3.46 (m 2H), 2.36 (sxt, 1H, J=7.0 Hz), 2.20 (sxt, 1H, J=7.0 Hz); $^{13}$C NMR (125 MHz, CD$_3$OD) δ 171.1, 52.6, 34.9, 28.5.

Example 4

Benzyl(S)-1-(methoxycarbonyl)-3-bromopropylcarbamate (6)

Referring to FIG. 2, (S)-2-Amino-4-bromobutanoic acid.HC/Br 5 (24 g, 0.091 mol) was dissolved in anhydrous methanol (150 mL) and the solution was chilled in an ice bath. Thionyl chloride (9.94 mL, 0.137 mol) was added dropwise with stirring over 0.5 hrs and the resulting mixture was allowed to warm the room temperature. After 18 hrs, the solvent was evaporated under reduced pressured. Ethyl acetate was then added to the orange oil concentrate to precipitate the methyl ester product. The fine white solid was collected by filtration and the liquor was subsequently evaporated giving again a orange viscous oil. Ethyl acetate was added to precipitate additional product and this process was repeated 6 times to provide 19.2 g (78.8%) of intermediate.

The esterified salt (19.0 g, 0.069 mol) was then added to an ice-chilled 2:1 mixture of distilled water:dichloromethane (90 mL) containing sodium bicarbonate (13.8 g, 0.165 mol) and carboxybenzyl chloride (13.82 g, 0.081 mol) was introduced dropwise to the vigorously stirred biphasic solution. After 15 hrs, the dichloromethane was evaporated and the pH of the aqueous layer was adjusted to 2.0 with 0.5 M HCl. The mixture was extracted 3 times with ethyl acetate, dried over magnesium sulfate, filtered, and concentrated to a highly viscous oil.

The benzyl(S)-1-(methoxycarbonyl)-3-bromopropylcarbamate 6 was purified by silica gel chromatography using first 9:1 hexanes:ethyl acetate to remove excess carboxybenzyl chloride and benzyl alcohol decomposed byproduct followed by 2:1 hexanes:ethyl acetate that produced benzyl(S)-1-(methoxycarbonyl)-3-bromopropylcarbamate 6 ($R_f$ 0.40) as a viscous oil (22.6 g, 0.068 mol, 98.2%) that slowly solidified to a pinkish, waxy solid with a m.p. of 57° C.-60° C. and a $[\alpha]^{26}$D=–40.0 (c 1, dimethylformamide) [lit$^{bartley}$: m.p.=61° C.; $[\alpha]^{25}$D –40.3° (c 1, dimethylformamide)].
$^1$H NMR (500 MHz, CDCl$_3$) δ 7.36-7.29 (m, 5H), 5.43 (d, 1H, J=7.5 Hz), 5.10 (s, 2H), 4.52-4.48 (m, 1H), 3.74 (s, 3H), 3.40 (t, 2H, J=7.0 Hz), 2.44-2.40 (m, 1H), 2.24-2.20 (m, 1H); $^{13}$C NMR (125 MHz, CDCl$_3$) δ 172.1, 156.0, 136.1, 128.5, 128.2, 128.1, 67.1, 52.8, 52.6, 35.3, 28.4; ESI-HRMS calculated for C$_{13}$H$_{16}$BrNO$_4$ [M+Na]$^+$ 352.0263, found 352.0164.

Example 5

S-Alkyl Homocysteine Sulfide Analogs (7a-7h)—General Synthesis Procedure

To a sealed tube containing benzyl(S)-1-(methoxycarbonyl)-3-bromopropylcarbamate 6 (0.50 g, 1.50 mmol), sodium iodide (66 mg, 0.44 mmol), and potassium carbonate (0.24 g, 1.75 mmol) was added 3 mol equiv of an alkyl or aryl thiol (4.5 mmol) in 10 mL of dry acetone. The containers were then tightly capped and stirred in a sand bath heated to 90° C.-95° C. for 16-20 hrs. After cooling to room temperature, the solutions were filtered, evaporated, redissolved in dichloromethane, washed with brine, dried over sodium sulphate, and concentrated. The resulting sulfides were purified by flash chromatography on a Biotage SP1™ implementing solvent gradients calculated by the system from the products' $R_f$ values as indicated below.

Example 6

Benzyl(S)-1-(methoxycarbonyl)-3-(ethylthio)propylcarbamate (7a)

Colorless oil; TLC (SiO$_2$) $R_f$ 0.41 (3:1 hexanes:ethyl acetate); $[\alpha]^{26}_D$ +18.5° (c 1, CHCl$_3$); $^1$H NMR (500 MHz, CDCl$_3$) δ 7.33-7.27 (m, 5H), 5.51 (d, 1H, J=7.5 Hz), 5.08 (ABq, 2H, J$_{AB}$=12.5 Hz), 4.49-4.45 (m, 1H), 3.71 (s, 3H), 2.53-2.46 (m, 4H), 2.13-2.07 (m, 1H), 1.96-1.88 (m, 1H), 1.20 (t, 3H, J=7.5 Hz); $^{13}$C NMR (125 MHz, CDCl$_3$) δ 172.6, 156.0, 136.3, 128.6, 128.3, 128.2, 67.2, 53.3, 52.6, 32.5, 27.3, 25.9, 14.7; ESI-HRMS calculated for C$_{15}$H$_{21}$NO$_4$S [M+H]$^+$ 312.1191, found 312.1266.

Example 7

Benzyl(S)-1-(methoxycarbonyl)-3-(propylthio)propylcarbamate (7b)

Colorless oil; TLC (SiO$_2$) $R_f$ 0.48 (3:1 hexanes:ethyl acetate); $[\alpha]^{26}_D$ +18.4° (c 1, CHCl$_3$); $^1$H NMR (500 MHz, CDCl$_3$) δ 7.33-7.27 (m, 5H), 5.51 (d, 1H, J=8.0 Hz), 5.08 (ABq, 2H, J$_{AB}$=12.5 Hz), 4.49-4.44 (m, 1H), 3.71 (s, 3H), 2.50 (t, 2H, J=7.5 Hz), 2.44 (t, 2H, J=7.5 Hz), 2.12-2.09 (m, 1H), 1.94-1.90 (m, 1H), 1.55 (sxt, 2H, J=7.5 Hz), 0.94 (t, 3H, J=7.5 Hz); $^{13}$C NMR (125 MHz, CDCl$_3$) δ 172.6, 156.0, 136.3, 128.6, 128.3, 128.2, 67.1, 53.3, 52.6, 34.2, 32.6, 27.7, 22.9, 13.6; ESI-HRMS calculated for C$_{16}$H$_{23}$NO$_4$S [M+H]$^+$ 326.1348, found 326.1426.

Example 8

Benzyl(S)-1-(methoxycarbonyl)-3-(isopropylthio) propylcarbamate (7c)

Colorless oil; TLC (SiO$_2$) R$_f$ 0.43 (3:1 hexanes:ethyl acetate); [α]$^{26}_D$ +18.1° (c 1, CHCl$_3$); $^1$H NMR (500 MHz, CDCl$_3$) δ 7.33-7.28 (m, 5H), 5.51 (d, 1H, J=8.0 Hz), 5.08 (ABq, 2H, J$_{AB}$=12.5 Hz), 4.49-4.45 (m, 1H), 3.72 (s, 3H), 2.89-2.85 (m, 1H), 2.53 (t, 2H), 2.14-2.07 (m, 1H), 1.96-1.89 (m, 1H), 1.22 (s, 3H), 1.21 (s, 3H); $^{13}$C NMR (125 MHz, CDCl$_3$) δ 172.6, 156.0, 136.3, 128.7, 128.3, 128.2, 67.2, 53.4, 52.6, 34.9, 32.8, 26.3, 23.4; ESI-HRMS calculated for C$_{16}$H$_{23}$NO$_4$S [M+H]$^+$ 326.1348, found 326.1429.

Example 9

Benzyl(S)-1-(methoxycarbonyl)-3-(butylthio)propyl-carbamate (7d)

Colorless oil; TLC (SiO$_2$) R$_f$ 0.48 (3:1 hexanes:ethyl acetate); [α]$^{26}_D$ +19.5° (c 0.8, CHCl$_3$); $^1$H NMR (500 MHz, CDCl$_3$) δ 7.34-7.27 (m, 5H), 5.51 (bs, 1H), 5.08 (app s, 2H), 4.49-4.45 (m, 1H), 3.71 (s, 3H), 2.50 (t, 2H, J=7.5 Hz), 2.46 (t, 2H, J=7.5 Hz), 2.14-2.07 (m, 1H), 1.95-1.88 (m, 1H), 1.51 (qnt, 2H, J=7.5 Hz), 1.36 (sxt, 2H, J=7.5 Hz), 0.88 (t, 3H, J=7.5 Hz); $^{13}$C NMR (125 MHz, CDCl$_3$) δ 172.6, 156.0, 136.3, 128.6, 128.3, 128.2, 67.2, 53.4, 52.6, 32.6, 31.9, 31.7, 27.8, 22.1, 13.8; ESI-HRMS calculated for C$_{17}$H$_{25}$NO$_4$S [M+H]$^+$ 340.1504, found 340.1593.

Example 10

Benzyl(S)-1-(methoxycarbonyl)-3-(hexylthio)propyl-carbamate (7f)

Colorless oil; TLC (SiO$_2$) R$_f$=0.52 (3:1 hexanes:ethyl acetate); [α]$^{26}_D$ +18.3° (c 0.7, CHCl$_3$); $^1$H NMR (500 MHz, CDCl$_3$) δ 7.34-7.27 (m, 5H), 5.53 (d, 1H, J=8 Hz), 5.03 (app s, 2H), 4.44-4.39 (m, 1H), 3.71 (s, 3H), 2.45 (t, 2H, J=7.5 Hz), 2.40 (t, 2H, J=7.5 Hz), 2.09-2.02 (m, 1H), 1.90-1.82 (m, 1H), 1.47 (qnt, 2H, J=7.5 Hz), 1.31-1.16 (m, 6H), 0.86 (t, 3H, J=7.0 Hz); $^{13}$C NMR (125 MHz, CDCl$_3$) δ 172.6, 156.0, 136.3, 128.6, 128.3, 128.2, 67.1, 53.3, 52.6, 32.5, 32.2, 31.5, 29.5, 28.6, 27.8, 22.6, 14.1; ESI-HRMS calculated for C$_{19}$H$_{29}$NO$_4$S [M+H]$^+$ 368.1817, found 368.1902.

Example 11

Benzyl(S)-1-(methoxycarbonyl)-3-(octylthio)propyl-carbamate (7g)

Colorless oil; TLC (SiO$_2$) R$_f$ 0.44 (3:1 hexanes:ethyl acetate); [α]$^{24}_D$ +17.0° (c 1.1, CHCl$_3$); $^1$C NMR (500 MHz, CDCl$_3$) δ 7.32-7.27 (m, 5H), 5.53 (d, 1H, J=8.5 Hz), 5.07 (app s, 2H), 4.48-4.44 (m, 1H), 3.71 (s, 3H), 2.50 (t, 2H, J=7.5 Hz), 2.45 (t, 2H, J=7.5 Hz), 2.14-2.07 (m, 1H), 1.95-1.89 (m, 1H), 1.55-1.49 (m, 2H), 1.33-1.24 (m, 10H), 0.85 (t, 3H, J=7.0 Hz); $^{13}$C NMR (125 MHz, CDCl$_3$) δ 172.6, 156.0, 136.3, 128.6, 128.3, 128.2, 67.1, 53.3, 52.6, 32.5, 32.2, 31.9, 29.6, 29.3, 29.0, 27.8, 22.7, 14.2; ESI-HRMS calculated for C$_{21}$H$_{33}$NO$_4$S [M+H]$^+$ 396.2130, found 396.2219.

Example 12

Benzyl(S)-1-(methoxycarbonyl)-3-(1-decylthio)pro-pylcarbamate (7h)

Colorless waxy solid; TLC (SiO$_2$) R$_f$ 0.57 (3:1 hexanes: ethyl acetate); [α]$^{23}_D$=+15.7° (c 1.4, CHCl$_3$); $^1$H NMR (500 MHz, CDCl$_3$) δ 7.33-7.27 (m, 5H), 5.48 (bs, 1H), 5.08 (s, 2H), 4.49-4.45 (m, 1H), 2.50 (t, 2H, J=7.5 Hz), 2.46 (t, 2H, J=7.5 Hz), 2.14-2.08 (m, 1H), 1.96-1.89 (m, 1H), 1.52 (qnt, 2H, J=7.5 Hz), 1.33-1.24 (m, 14H), 0.86 (t, 3H, J=7.0 Hz); $^{13}$C NMR (125 MHz, CDCl$_3$) δ 172.6, 156.0, 136.3, 128.7, 128.3, 128.2, 67.2, 53.4, 52.6, 32.6, 32.2, 32.0, 29.7, 29.4, 29.0, 27.9, 22.8, 14.2; ESI-HRMS calculated for C$_{23}$H$_{37}$NO$_4$S [M+H]$^+$ 424.2443, found 424.2532.

Example 13

S-Alkyl Homocysteine Sulfoxide Analogs (8a-8g)—General Synthesis Procedure

Referring to FIG. 2, to a stirring ice-chilled methanol (10 mL) solution of a sulfide selected from 7a-7h (0.9-1.5 mmol) was added sodium periodate (1.02 mol equiv) in 3 mL of water. After 10 h, the solutions were filtered and the methanol was evaporated under reduced pressure. Brine was then added and the products were extracted twice with dichloromethane. The combined organic phases were next dried over sodium sulfate, filtered, and concentrated. The crude sulfoxides (8a-8g) were purified by flash chromatography on a Biotage SP1™ implementing solvent gradients calculated by the system from the products' R$_f$ values indicated below.

Example 14

Benzyl(S)-1-(methoxycarbonyl)-3-(ethylsulfinyl) propylcarbamate (8a)

Colorless oil (diastereomer mixture); TLC (SiO$_2$) Rf 0.57 (9:1 dichloromethane:methanol); $^1$H NMR (500 MHz, CDCl$_3$) δ 7.35-7.28 (m, 10H), 5.79 (d, 1H, J=7.0 Hz), 5.69 (d, 1H, J=7.5 Hz), 5.08 (s, 4H), 4.48-4.45 (m, 2H), 3.74 (s, 6H), 2.75-2.60 (m, 8H) 2.37-2.33 (m, 2H), 2.17-2.14 (m, 12H), 1.29-1.26 (m, 6H); $^{13}$C NMR (125 MHz, CDCl$_3$) δ 172.0, 156.2, 136.2, 128.8, 128.7, 128.5, 128.4, 128.3, 67.4, 53.3, 53.0, 47.5, 46.0, 26.5, 26.2, 7.0; ESI-HRMS calculated for C$_{15}$H$_{21}$NO$_5$S [M+H]$^+$ 328.1140, found 328.1227

Example 15

Benzyl(S)-1-(methoxycarbonyl)-3-(propylsulfinyl) propylcarbamate (8b)

Pale yellow oil (diastereomer mixture); TLC (SiO$_2$) R$_f$ 0.28 (100% ethyl acetate); $^1$H NMR (500 MHz, CDCl$_3$) δ 7.28-7.23 (m, 10H), 6.41 (d, 1H, J=8.0 Hz), 6.38 (d, 1H, J=8.0 Hz), 5.04 (app s, 4H), 4.39-4.36 (m, 2H), 3.66 (s, 6H), 2.68-2.59 (m, 6H), 2.5-2.45 (m, 2H), 2.29-2.25 (m, 2H), 2.11-2.05 (m, 2H), 1.7-1.66 (m, 4H), 0.97 (t, 6H, J=7.0 Hz); $^{13}$C NMR (125 MHz, CDCl$_3$) δ 171.8, 156.2, 136.1, 128.3, 128.0, 127.9, 66.8, 54.0, 53.9, 53.1, 52.8, 52.4, 47.9, 47.8, 25.5, 25.3, 16.1, 13.2; ESI-HRMS calculated for C$_{16}$H$_{23}$NO$_5$S [M+H]$^+$ 342.1297, found 342.1377.

Example 16

Benzyl(S)-1-(methoxycarbonyl)-3-(isopropylsulfinyl)propylcarbamate (8c)

Colorless oil (diastereomer mixture); TLC (SiO$_2$) R$_f$ 0.21 (1:1 hexanes:ethyl acetate); $^1$H NMR (500 MHz, CDCl$_3$) δ 7.32-7.27 (m, 10H), 5.91 (d, 1H, J=8.0 Hz), 5.80 (d, 1H, J=8.0 Hz), 5.07 (app s, 4H), 4.46-4.43 (m, 2H), 3.72 (s, 6H), 2.74-2.64 (m, 4H), 2.60-2.54 (m, 2H), 2.34 (m, 2H), 2.14-2.08 (m, 2H), 1.24 (d, 6H, J=7.0 Hz), 1.18 (d, 6H, J=7.0 Hz); $^{13}$C NMR (125 MHz, CDCl$_3$) δ 172.0, 170.8, 156.3, 136.3, 128.6, 128.7, 128.3, 128.2, 67.2, 64.1, 53.4, 53.1, 52.9, 52.4, 50.7, 44.7, 26.6, 26.3, 15.1, 15.0; ESI-HRMS calculated for C$_{16}$H$_{23}$NO$_5$S [M+H]$^+$ 342.1297, found 342.1372

Example 17

Benzyl(S)-1-(methoxycarbonyl)-3-(butylsulfinyl)propylcarbamate (8d)

Colorless oil (diastereomer mixture); TLC (SiO$_2$) R$_f$ 0.20 (1:1 hexanes:ethyl acetate); $^1$H NMR (500 MHz, CDCl$_3$) δ 7.31-7.26 (m, 10H), 6.28 (d, 1H, J=8.0 Hz), 6.23 (d, 1H, J=8.0 Hz), 5.07 (s, 4H), 4.45-4.38 (m, 2H), 3.69 (s, 6H), 2.73-2.54 (m, 8H), 2.33-2.30 (m, 2H), 2.16-2.07 (m, 2H), 1.68-1.64 (m, 4H), 1.47-1.34 (m, 4H), 0.91 (t, 6H, J=7.5 Hz); $^{13}$C NMR (125 MHz, CDCl$_3$) δ 171.9, 156.2, 136.2, 128.4, 128.1, 128.0, 66.9, 53.2, 52.9, 52.6, 52.0, 48.0, 47.9, 25.8, 25.6, 24.5, 21.9, 13.6; ESI-HRMS calculated for C$_{17}$H$_{25}$NO$_5$S [M+H]$^+$ 356.1453, found 356.1544.

Example 18

Benzyl(S)-1-(methoxycarbonyl)-3-(1-hexylsulfinyl)propylcarbamate (8e)

Pale yellow oil (diastereomer mixture); TLC (SiO$_2$) R$_f$ 0.21 (1:1 hexanes:ethyl acetate); $^1$H NMR (500 MHz, CDCl$_3$) δ 7.34-7.27 (m, 10H), 5.87 (d, 1H, J=8.0 Hz), 5.77 (d, 1H, J=8.0 Hz), 5.07 (s, 4H), 4.48-4.41 (m, 2H), 3.72 (s, 6H), 2.74-2.53 (m, 8H), 2.38-2.31 (m, 2H), 2.17-2.07 (m, 2H), 1.71-1.66 (m, 4H), 1.45-1.23 (m, 12H), 0.86 (t, 6H, J=7.0 Hz); $^{13}$C NMR (125 MHz, CDCl$_3$) δ 172.0, 156.2, 136.3, 136.2, 128.7, 128.4, 128.3, 67.3, 53.3, 53.0, 52.9, 52.7, 48.2, 48.1, 31.5, 28.6, 26.4, 26.1, 22.7, 22.5, 14.1; ESI-HRMS calculated for C$_{19}$H$_{29}$NO$_5$S [M+H]$^+$ 384.1766, found 384.1846.

Example 19

Benzyl(S)-1-(methoxycarbonyl)-3-(1-octylsulfinyl)propylcarbamate (8f)

White waxy solid (diastereomer mixture); m.p. 50° C.-52° C.; TLC (SiO$_2$) R$_f$ 0.30 (1:1 hexanes:ethyl acetate); $^1$H NMR (500 MHz, CDCl$_3$) δ 7.32-7.26 (m, 10H), 5.91 (d, 1H, J=8.0 Hz), 5.82 (d, 1H, J=8.0 Hz), 5.07 (s, 4H), 4.46-4.42 (m, 2H), 3.71 (s, 6H), 2.71-2.52 (m, 8H), 2.34-2.30 (m, 2H), 2.15-2.09 (m, 2H), 1.68-1.66 (m, 4H), 1.42-1.32 (m, 4H), 1.26-1.23 (m, 16H), 0.84 (t, 6H, J=7.0 Hz); $^{13}$C NMR (125 MHz, CDCl$_3$) δ 172.0, 156.2, 136.2, 128.7, 128.4, 128.3, 128.2, 67.2, 53.3, 53.0, 52.9, 52.7, 48.2, 48.1, 31.9, 29.3, 29.1, 28.9, 26.3, 26.0, 22.7, 14.2; ESI-HRMS calculated for C$_{21}$H$_{33}$NO$_5$S [M+H]$^+$ 412.2079, found 412.2174.

Example 20

Benzyl(S)-1-(methoxycarbonyl)-3-(1-decylsulfinyl)propylcarbamate (8g)

Soft white solid (diastereomer mixture); mp 66° C.-70° C.; TLC (SiO$_2$) R$_f$ 0.30 (1:1 hexanes:ethyl acetate); $^1$H NMR (500 MHz, CDCl$_3$) δ 7.29-7.22 (m, 10H), 6.45 (d, 1H, J=8.0 Hz), 6.41 (d, 1H, J=8.0 Hz), 5.03 (s, 4H), 4.37-4.34 (m, 2H), 3.64 (s, 6H), 2.68-2.60 (m, 6H), 2.52-2.47 (m, 2H), 2.28-2.25 (m, 2H), 2.10-2.04 (m, 2H), 1.63-1.60 (m, 4H), 1.23-1.20 (m, 28H), 0.82 (t, 6H, J=7.0 Hz); $^{13}$C NMR (125 MHz, CDCl$_3$) δ 171.8, 156.2, 156.1, 136.1, 128.3, 127.9, 66.7, 53.0, 52.8, 52.3, 52.1, 47.9, 47.8, 31.7, 29.3, 29.2, 29.1, 29.0, 28.6, 25.5, 25.3, 22.5, 22.4, 14.0; ESI-HRMS calculated for C$_{23}$H$_{37}$NO$_5$S [M+H]$^+$ 440.2392, found 440.2482

Example 21

S-Aryl Homocysteine Sulfide Analogs (9a-9f)—General Synthesis Procedure

Referring now to FIG. 3, Aryl sulfides 9a-9f were prepared from bromide 3 in a manner similar to the procedure detailed for sulfides 7a-7h with the exception that 1.2 mol equiv of thiophenols were used.

Example 22

Benzyl(S)-1-(methoxycarbonyl)-3-(benzylthiol)propylcarbamate (9a)

Colorless oil; TLC (SiO$_2$) R$_f$=0.40 (3:1 hexanes:ethyl acetate); product was indiscernible from bromide 6 by TLC. The mixture was isolated by chromatography and used in the subsequent m-CPBA oxidation reaction to provide sulfoxide 10a in 54.1% yield (308 mg, 0.74 mmol) in two steps.

Example 23

Benzyl(S)-1-(methoxycarbonyl)-3-(phenylthio)propylcarbamate (9b)

White waxy solid; m.p. 47° C.-48° C.; TLC (SiO$_2$) R$_f$ 0.37 (3:1 hexanes:ethyl acetate); [α]$^{22}_D$ +19.2° (c 1, CHCl$_3$); $^1$H NMR (500 MHz, CDCl$_3$) δ 7.40-7.30 (m, 8H), 7.23 (tt, 2H, J=7.0, 1.5 Hz), 5.66 (d, 1H, J=8.0 Hz), 5.16 (ABq, 2H, J$_{AB}$=12.3 Hz), 4.59-4.55 (m, 1H), 3.75 (s, 3H), 2.98 (t, 2H, J=7.5 Hz), 2.25-2.18 (m, 1H), 2.05-1.98 (m, 1H); $^{13}$C NMR (125 MHz, CDCl$_3$) δ 172.4, 156.0, 136.2, 135.6, 129.6, 129.1, 128.6, 128.3, 128.2, 126.4, 67.1, 53.2, 52.6, 32.2, 29.7; ESI-HRMS calculated for C$_{19}$H$_{21}$NO$_4$S [M+H]$^+$ 360.1191, found 360.1281.

Example 24

Benzyl(S)-1-(methoxycarbonyl)-3-(4-methoxyphenylthio)propylcarbamate (9c)

White waxy solid; m.p. 36° C.-37° C.; TLC (SiO$_2$) R$_f$ 0.37 (3:1 hexanes:ethyl acetate); [α]$^{26}_D$ +11.3° (c 0.9, CHCl$_3$); $^1$H NMR (500 MHz, CDCl$_3$) δ 7.35-7.28 (m, 5H), 6.83-6.80 (m, 2H), 5.41 (d, 1H, J=8.5 Hz), 5.08 (ABq, 2H, J$_{AB}$=12.3 Hz), 4.51-4.47 (m, 1H), 3.77 (s, 3H), 3.70 (s, 3H), 2.81 (t, 2H, J=7.5 Hz), 2.12-2.05 (m, 1H), 1.91-1.84 (m, 1H); $^{13}$C NMR (125 MHz, CDCl$_3$) δ 172.6, 159.3, 156.0, 136.3, 133.9, 128.7, 128.4, 128.3, 125.5, 114.8, 67.2, 55.5, 53.2, 52.7, 32.5, 32.0; ESI-HRMS calculated for $C_{20}H_{23}NO_5S$ [M+H]$^+$ 390.1297, found 390.1390.

Example 25

Benzyl(S)-1-(methoxycarbonyl)-3-(4-chlorophenylthio)propylcarbamate (9d)

White waxy solid; m.p. 48° C.-49° C.; TLC (SiO$_2$) R$_f$ 0.42 (3:1 hexanes:ethyl acetate); [α]$^{26}_D$ +15.2° (c 1.1, CHCl$_3$); $^1$H NMR (500 MHz, CDCl$_3$) δ 7.41-7.35 (m, 5H), 7.28 (m, 4H), 5.51 (d, 1H, J=8 Hz), 5.15 (ABq, 2H, J$_{AB}$=12.5 Hz), 4.58-5.43 (m, 1H), 3.76 (s, 3H), 2.95 (app t, 2H, J=7.0 Hz), 2.21-2.16 (m, 1H), 2.02-1.96 (m, 1H); $^{13}$C NMR (125 MHz, CDCl$_3$) δ 172.4, 156.1, 136.2, 134.2, 132.6, 131.2, 129.3, 128.8, 128.3, 67.4, 53.2, 52.8, 32.4, 30.2; ESI-HRMS calculated for $C_{19}H_{20}ClNO_4S$ [M+H]$^+$ 394.0802, found 394.0874.

Example 26

Benzyl(S)-1-(methoxycarbonyl)-3-(4-nitrophenylthiol)propylcarbamate (9e)

Orange semi-solid; TLC (SiO$_2$) R$_f$ 0.32 (3:1 hexanes:ethyl acetate); [α]$^{26}_D$ +11.6° (c 0.7, CHCl$_3$); $^1$H NMR (500 MHz, CDCl$_3$) δ 8.01 (d, 2H, J=10.5 Hz), 7.28-7.18 (m, 7H), 5.51 (d, 1H, J=7.5 Hz), 5.07 (ABq, 2H, J$_{AB}$=12.3 Hz), 4.49-4.45 (m, 1H), 3.67 (s, 3H), 3.00-2.93 (m, 2H), 2.20-2.16 (m, 1H), 2.01-1.93 (m 1H); $^{13}$C NMR (125 MHz, CDCl$_3$) δ 172.1, 156.1, 146.7, 145.3, 136.1, 128.7, 128.5, 124.2, 67.4, 53.2, 52.9, 31.9, 28.0; ESI-HRMS calculated for $C_{19}H_{20}N_2O_6S$ [M+H]$^+$ 405.1042, found 405.1126.

Example 27

Benzyl(S)-1-(methoxycarbonyl)-3-(2-nitrophenylthiol)propylcarbamate (9f)

Yellow solid; m.p. 78° C.-80° C.; TLC (SiO$_2$) R$_f$ 0.32 (3:1 hexanes:ethyl acetate); [α]$^{27}_D$ +37.7° (c 0.8, CHCl$_3$); $^1$H NMR (500 MHz, CDCl$_3$) δ 8.21 (d, 1H, J=8.5 Hz), 7.55 (t, 1H, J=7.5 Hz), 7.38-7.36 (m, 6H), 7.28 (t, 1H, J=7.5 Hz), 5.63 (d, 1H, J=7 Hz), 5.17-5.12 (m, 2H), 4.57-4.56 (m, 1H), 3.78 (s, 3H), 3.06-2.96 (m, 2H), 2.34-2.33 (m, 1H) 2.11-2.07 (m, 2H); $^{13}$C NMR (125 MHz, CDCl$_3$) δ 172.1, 156.1, 146.3, 137.0, 136.2, 133.8, 128.7, 128.4, 128.3, 126.6, 126.4, 124.9, 67.4, 53.5, 52.9, 31.2, 28.2; ESI-HRMS calculated for $C_{19}H_{20}N_2O_6S$ [M+H]$^+$ 405.1042, found 405.1122.

Example 28

S-Aryl Homocysteine Sulfoxide Analogs (10a-10f)—General Synthesis Procedure

To a stirring ice-chilled dichloromethane (10 mL) solution of a sulfide selected from 9a-9f (0.7-2.1 mmol) was added m-CPBA (1.25 mol equiv) in 5 mL of dichloromethane. After 1 hr, the reactions were quenched with 5% sodium bicarbonate (20 mL) and extracted twice with dichloromethane. The combined organic extracts were then dried over sodium sulfate, filtered, and concentrated. The crude sulfoxides 10a-10f were purified by flash chromatography on a Biotage SP1™ implementing solvent gradients calculated by the system from the products' R$_f$ values indicated below.

Example 29

Benzyl(S)-1-(methoxycarbonyl)-3-(benzylsulfinyl)propylcarbamate (10a)

Thick beige oil (diastereomer mixture); TLC (SiO$_2$) R$_f$ 0.48 (100% ethyl acetate); $^1$H NMR (500 MHz, CDCl$_3$) δ 7.39-7.36 (m, 16H), 7.30-7.28 (m, 4H), 5.72 (d, 1H, J=7.5 Hz), 5.63 (d, 1H, J=7.5 Hz), 5.13 (app s, 6H), 4.52-4.46 (m, 2H), 4.07-4.02 (m, 2H), 3.97-3.95 (m, 2H), 3.77 (s, 6H), 2.77-2.67 (m, 3H), 2.61-2.55 (m, 1H), 2.40-2.37 (m, 2H), 2.22-2.12 (m, 2H); $^{13}$C NMR (125 MHz, CDCl$_3$) δ 171.8, 156.2, 136.2, 130.1, 129.6, 129.0, 128.6, 128.5, 128.3, 128.1, 67.1, 58.0, 53.1, 52.9, 52.7, 46.5, 25.7, 25.4; ESI-HRMS calculated for $C_{20}H_{23}NO_5S$ [M+H]$^+$ 390.1297, found 390.1376.

Example 30

Benzyl(S)-1-(methoxycarbonyl)-3-(phenylsulfinyl)propylcarbamate (10b)

Thick beige oil/solid (diastereomer mixture); TLC (SiO$_2$) R$_f$ 0.25 (1:1 hexanes:ethyl acetate); $^1$H NMR (500 MHz, CDCl$_3$) δ 7.53-7.45 (m, 10H), 7.32-7.26 (m, 10H), 5.89 (d, 1H, J=8.0 Hz), 5.82 (d, 1H, J=8.0 Hz), 5.05 (ABq, 4H, J$_{AB}$=13 Hz), 4.45-4.41 (m, 1H), 4.37-4.33 (m, 1H), 3.68 (s, 3H), 3.66 (s, 3H), 2.96-2.86 (m, 2H), 2.82-2.68 (m, 2H), 2.34-2.29 (m, 1H), 2.13-2.07 (m, 2H), 1.91-1.87 (m, 1H); $^{13}$C NMR (125 MHz, CDCl$_3$) δ 172.0, 171.9, 156.2, 143.0, 136.2, 131.3, 131.2, 129.4, 128.6, 128.3, 128.2, 124.1, 67.2, 53.1, 52.8, 52.7, 52.6, 25.5, 25.0; ESI-HRMS calculated for $C_{19}H_{21}NO_5S$ [M+H]$^+$ 375.1140, found 375.1217.

Example 31

Benzyl(S)-1-(methoxycarbonyl)-3-(4-methoxyphenylsulfinyl)propylcarbamate (10c)

Pale yellow oil (diastereomer mixture); TLC (SiO$_2$) R$_f$ 0.21 (1:1 hexanes:ethyl acetate); $^1$H NMR (500 MHz, CDCl$_3$) δ 7.48 (d, 4H, J=8.0 Hz), 7.32-7.29 (m, 10H), 6.98 (m, 4H), 5.67 (d, 1H, J=8 Hz), 5.61 (d, 1H, J=8.0 Hz), 5.07 (ABq, 4H, J$_{AB}$=13.0 Hz), 4.45-4.44 (m, 1H), 4.39-4.38 (m, 1H), 3.83 (s, 6H), 3.72 (s, 3H), 3.70 (s, 3H) 2.9-2.68 (m, 4H), 2.29 (m, 1H), 2.15-2.02 (m, 2H), 1.94-1.87 (m, 1H); $^{13}$C NMR (125 MHz, CDCl$_3$) δ 172.0, 171.9, 162.1, 162.0, 156.2, 136.2, 133.7, 128.6, 128.2, 128.1, 126.0, 115.0, 67.1, 55.6, 53.1, 52.8, 25.4, 25.0; ESI-HRMS calculated for $C_{20}H_{23}NO_6S$ [M+H]$^+$ 406.1246, found 406.1340.

Example 32

Benzyl(S)-1-(methoxycarbonyl)-3-(4-chlorophenylsulfinyl)propylcarbamate (10d)

Pale yellow oil (diastereomer mixture); TLC (SiO$_2$) R$_f$ 0.39 (1:1 hexanes:ethyl acetate); $^1$H NMR (500 MHz, CDCl$_3$) δ 7.51-7.44 (m, 8H), 7.33 (m, 10H), 6.06 (d, 1H, J=8.0 Hz), 6.01 (d, 1H, J=8.5 Hz), 5.12-5.05 (m, 4H), 4.50-4.46 (m, 1H), 4.42-4.38 (m, 1H), 3.72 (s, 3H), 3.70 (s, 3H), 2.99-2.90 (m, 2H) 2.83-2.71 (m, 2H), 2.38-2.31 (m, 1H), 2.15-2.09 (m, 2H), 1.92-1.88 (m, 1H); $^{13}$C NMR (125 MHz, CDCl$_3$) δ 171.7, 156.1, 141.4, 141.3, 137.1, 136.1, 129.5, 129.4, 128.4, 128.1, 128.0, 125.4, 66.9, 52.9, 52.7, 52.6, 52.5, 25.0, 24.5; ESI-HRMS calculated for $C_{19}H_{20}ClNO_5S$ [M+H]$^+$ 410.0751, found 410.0847.

Example 33

Benzyl(S)-1-(methoxycarbonyl)-3-(4-nitrophenyl-sulfinyl)propylcarbamate (10e)

Yellow oil (diastereomer mixture); TLC (SiO$_2$) R$_f$ 0.16 (1:1 hexanes:ethyl acetate); $^1$H NMR (500 MHz, CDCl$_3$) δ 8.34-8.30 (m, 4H), 7.75-7.71 (m, 4H), 7.34-7.32 (m, 10H), 5.64 (d, 1H, J=8.0 Hz), 5.58 (d, 1H, J=8.0 Hz), 5.07 (ABq, 4H, J$_{AB}$=11.5 Hz), 4.52 (m, 1H), 4.40 (m, 1H), 3.74 (s, 3H), 3.72 (s, 3H), 3.03-2.98 (m, 2H), 2.83-2.82 (m, 1H) 2.76-2.75 (m, 1H), 2.47-2.45 (m, 1H), 2.18-2.11 (m, 2H), 1.88-1.84 (m, 1H); $^{13}$C NMR (125 MHz, CDCl$_3$) δ 171.7, 171.6, 165.8, 156.3, 150.8, 149.7, 136.1, 128.8, 128.6, 128.3, 125.3, 124.6, 67.5, 53.4, 53.1, 52.9, 52.6, 26.3; ESI-HRMS calculated for C$_{19}$H$_{20}$N$_2$O$_7$S [M+H]$^+$ 405.10421, found 405.1122

Example 34

Benzyl(S)-1-(methoxycarbonyl)-3-(2-nitrophenyl-sulfinyl)propylcarbamate (10f)

Yellow solid (diastereomer mixture); m.p. 103° C.-109° C.; TLC (SiO$_2$) R$_f$ 0.22 (1:1 hexanes:ethyl acetate); $^1$H NMR (500 MHz, CDCl$_3$) δ 8.32 (d, 2H, J=8.0 Hz), 8.26 (d, 2H, J=8.0 Hz), 7.93 (td, 2H, J=7.5, 3.5 Hz), 7.72 (t, 2H, J=7.5 Hz), 7.36-7.30 (m, 10H), 5.86 (d, 1H, J=8.5 Hz), 5.81 (d, 1H, J=8.5 Hz), 5.81 (os, 4H), 4.89-4.45 (m, 1H), 4.43-4.38 (m, 1H), 3.74 (s, 3H), 3.38-3.26 (m, 2H), 2.95-2.82 (m, 2H), 2.59-2.54 (m, 1H), 2.34-2.25 (m, 2H), 2.07-2.05 (m, 1H); $^{13}$C NMR (125 MHz, CDCl$_3$) δ 171.9, 156.1, 144.2, 142.5, 136.2, 135.6, 131.8, 128.6, 128.2, 127.0, 125.5, 67.2, 53.0, 52.8, 52.1, 51.6, 26.1, 25.8; ESI-HRMS calculated for C$_{19}$H$_{20}$N$_2$O$_7$S [M+H]$^+$ 421.0991, found 421.1079

Example 35

Thermolysis of Sulfoxides 8a-8f—General Procedure

To a 25 mL pear-shaped flask was added a sulfoxide selected from 8a-8f (0.1 mmol) and a stir vane. The flask was capped and stirred in an oil bath heated to 145° C. The dark crude residue was then purified by flash chromatography on a Biotage SP1™ implementing solvent gradients calculated by the system from the R$_f$ value of Cbz-vinylglycine-OMe (0.55, 3:1 hexanes:ethyl acetate).

Example 36

Preparation of 2-Nitrothiophenol (11)

Figure 4:
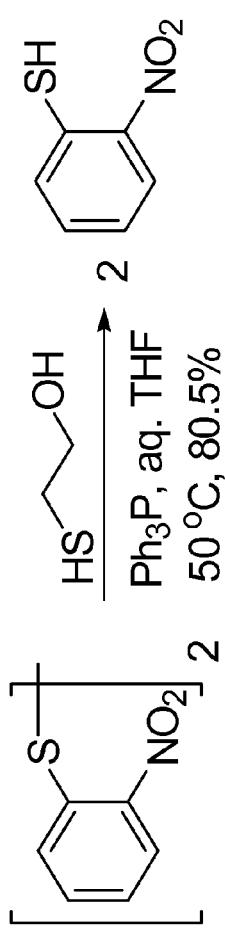
FIG. 4 is a schematic showing the synthesis of o-nitrothiophenol 11 from its disulphide.

Referring now to FIG. 4, to a suspension of 2-nitrophenyl disulfide (0.805 g, 2.61 mmol) in 20 mL of degassed tetrahydrofuran was added triphenylphosphine (1.03 g, 3.92 mmol), 2-mercaptoethanol (184 μl, 2.61 mmol), and 470 μL of distilled water (26.1 mmol). The solution was stirred at 50° C. for 16 hrs then cooled to room temperature and the precipitated triphenylphosphine oxide was removed by vacuum filtration through celite. The filtrate was concentrated, redissolved in dichloromethane, washed with distilled water and brine, dried over sodium sulfate, and evaporated. The resulting thick pungent orange oil was subject to flash chromatography (4:1 hexanes:ethyl acetate) and pure 2-nitrothiophenol 11 (653 mg, 4.21 mmol) was isolated in 80.5% yield from the bright yellow band fractions. m.p. 40° C.-42° C.

Example 37

Conversion of benzyl(S)-1-(methoxycarbonyl)-3-(2-nitrophenylsulfinyl)propylcarbamate (10f) to Cbz-vinylglycine-OMe (−)-1 Under Reflux (Mild Thermolysis)

Sulfoxide 10f was refluxed in a nonpolar, aprotic solvent (except toluene) until completely converted to the product. The solution was then cooled to room temperature and the precipitated byproduct was removed by vacuum filtration. After the flask was rinsed with 1:1 hexanes:ethyl acetate and filtered, the solvent was evaporated under reduced pressure to provide the product.

Example 38

Preparation of Cbz-VG-Phe-OMe (13)

Referring now to FIG. 6, to a suspended mixture of acid 12 (44.5 mg, 0.11 mmol), HOBt (14.8 mg, 0.11 mmol), Phe-OMe.HCl (23.7 mg, 0.11 mmol) in MeCN (5 mL) was added EDC (21.5 mg, 0.12 mmol). After 15 min, DIPEA (21 L, 0.12 mmoL) was added and the Phe-OMe.HCl began to dissolve. The reaction was monitored by TLC and upon completion, the mixture was concentrated, redissolved in DCM, was washed sequentially with 1N HCl, brine, and 5% NaHCO$_3$, dried over Na$_2$SO$_4$, filtered, and concentrated under vacuum to provide the pure sulfoxide (56.3 mg, 0.10 mmol) in 90.4% yield as a yellow oil (diastereomer mixture); TLC (SiO$_2$) R$_f$ 0.77 (9:1 DCM:MeOH).

$^1$H NMR (500 MHz, CDCl$_3$) δ 8.25-8.23 (m, 2H), 8.17-8.14 (m, 2H), 7.87-7.83 (m, 2H), 7.65-7.61 (m, 2H), 7.26-7.09 (m, 20H), 6.80 (d, 1H, J=6.5 Hz), 6.73 (d, 1H, J=7.5 Hz), 5.29 (d, 1H, J=7.0 Hz), 5.25 (d, 1H, J=7.0 Hz), 5.01-4.95 (m, 4H), 4.52-4.48 (m, 2H), 4.39-4.35 (m, 2H), 3.64 (s, 6H), 3.16-2.98 (m, 6H), 2.74-2.68 (m, 2H), 2.42 (m, 1H), 2.19 (m, 2H), 2.00-1.96 (m, 2H).

The sulfoxide intermediate (24 mg, 0.04 mmol) was then refluxed for 24 hrs in toluene. The solution was then cooled to room temperature, filtered through celite, and concentrated. The crude dipeptide was then purified by flash chromatography on a BIOTAGE SP1™ to give pure vinylglycine dipeptide 13 (7.3 mg, 0.02 mmol) in 43.7% yield as a colorless oil.

$^1$H NMR (500 MHz, CDCl$_3$) δ 7.30-7.17 (m, 8H), 7.00 (d, 2H, J=7.0 Hz), 6.27 (d, 1H, J=6.0 Hz), 5.79-7.72 (m, 1H), 5.54 (bs, 1H), 5.32-5.23 (m, 2H), 5.04 (s, 3H). 4.80-4.76 (m, 1H), 4.62 (m, 1H), 3.05 (dq, 2H, J=5.0, 14.0 Hz).

Example 39

Preparation of Cbz-Phe-VG-OMe (16) Via Amine 13

Referring now to FIG. 6, the amine salt 13 (57 mg, 0.16 mmol) prepared by acid hydrolysis in 33% HBr/AcOH was added to dry MeCN (3 mL) containing HOBt (21 mg, 0.16 mmol), and Cbz-Phe-OH (47 mg, 0.16 mmol). To this stirring suspension was added EDC (30.5 mg, 0.17 mmol) following by DIPEA (28 μL, 0.16 mmol) after 3 mins. The reaction was monitored by TLC and upon completion, DCM was added and washed sequentially with 1N HCl, brine, and 5% NaHCO$_3$, dried over Na$_2$SO$_4$, filtered, and concentrated under vacuum to provide the pure dipeptide (53.1 mg, 0.84 mmol) as a yellow solid in 51.4% yield. This intermediate (27 mg, 0.05 mmol) was then oxidized with m-CPBA (11 mg, 0.6 mmol) in DCM at 5° C. and refluxed overnight in toluene. The vinyl dipeptide was purified on BIOTAGE SP1™ to give Cbz-Phe-VG-OMe 16 (5.3 mg, 0.01 mmol) in 27.3% yield.

$^1$H NMR (500 MHz, CDCl$_3$) δ 7.39-7.22 (m, 10H), 6.53 (bs, 1H), 5.84 (m, 1H), 5.34 (m, 1H), 5.27-5.24 (m, 2H), 5.13-5.08 (m, 3H), 4.53 (d, 1H, J=2.8 Hz), 3.76 (s, 3H), 3.16-3.08 (m, 2H); $^{13}$C NMR (125 MHz, CDCl$_3$) δ 170.6, 170.4, 156.1, 136.3, 131.2, 129.6, 128.9, 128.8, 128.6, 128.4, 128.3, 127.3, 118.3, 67.4, 56.3, 54.7, 53.0, 38.5, 29.1.

Example 40

Preparation of Cbz-Phe-VG-OMe (16) from Sulfoxide 15

The TFA salt of sulfoxide 15 (30 mg, 0.08 mmol) prepared by acid hydrolysis with 10% TFA in DCM was added to dry MeCN (3 mL) containing HOBt (10.5 mg, 0.08 mmol), and Cbz-Phe-OH (23.3 mg, 0.08 mmol). To this stirring suspension was added EDC (15.2 mg, 0.08 mmol) following by DIPEA (14 µl, 0.08 mmol) after 3 mins. The reaction was monitored by TLC and upon completion, DCM was added and washed sequentially with 1N HCl, brine, and 5% NaHCO$_3$, dried over Na$_2$SO$_4$, filtered, and concentrated under vacuum to provide the pure dipeptide (24.5 mg, 0.04 mmol) as a yellow solid in 55.4% yield. The intermediate was then reflux in toluene and purified on Biotage™ to give pure vinylglycine dipeptide 16.

Example 41

Conversion of 10f to Acid 12

The elimination reaction was also evaluated using excess sodium acetate to neutralize the precipitated sulfenic acid byproduct. Unlike previous bases, sodium acetate did not cause isomerization of vinylglycine, and completely neutralized the sulfenic acid 12.

Sulfoxide 10f (51 mg, 0.12 mmol) was refluxed for 0.5 h in a 1:1 solution of 5% HCl in AcOH. The AcOH was the evaporated under vacuum and the HCl portion was diluted with water then extracted three times with EtOAc. The combined EtOAc fractions were dried over MgSO$_4$, filtered and concentrated to provide acid 12 as a yellow solid in 63.3% crude yield.

Figure 7:
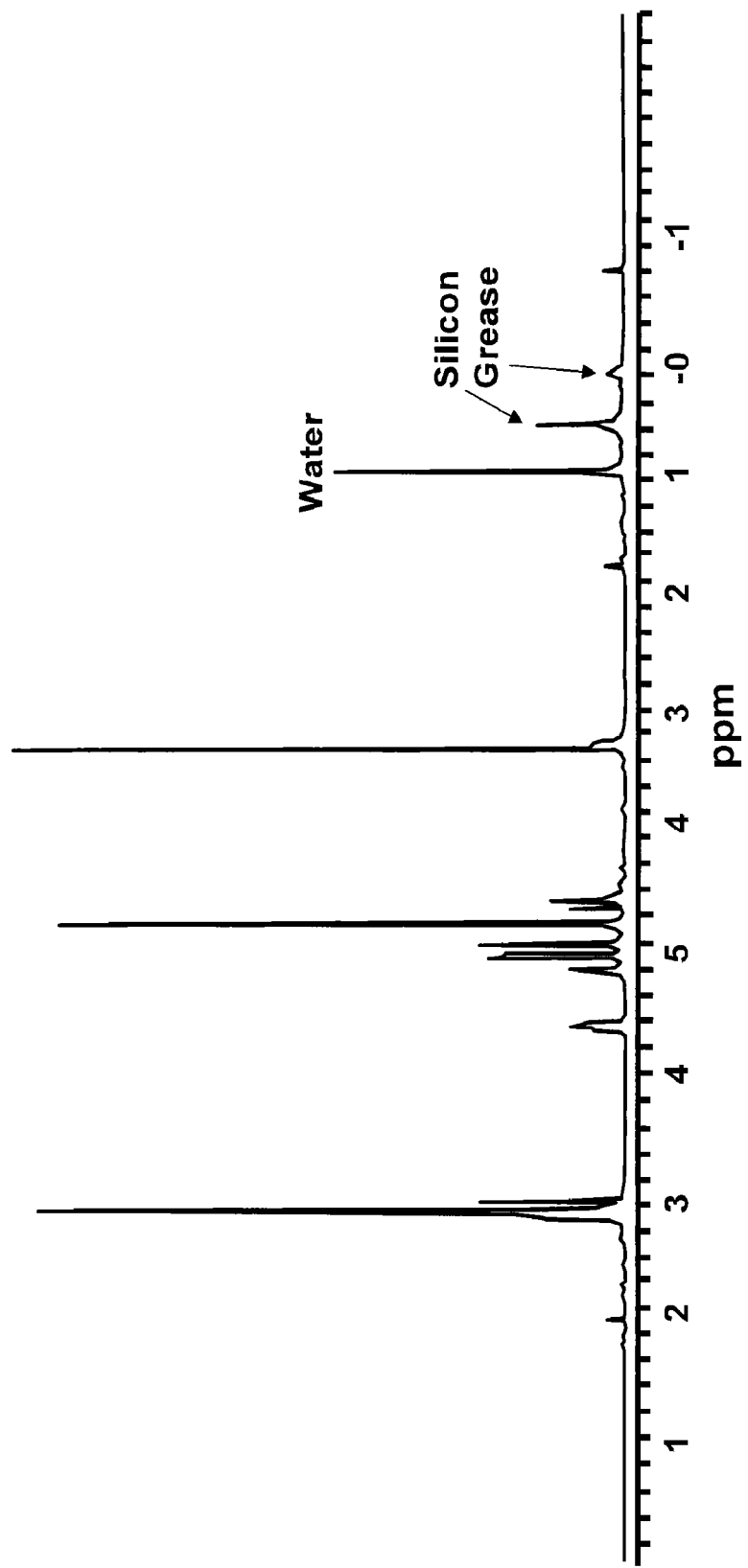
FIG. 7 is an image of an NMR output of the product from the protocol described in Example 42 below.

Under 6 hrs toluene reflux with 20 eq. of sodium acetate and after filtration of the solution, the NMR of the crude product was as shown in FIG. 7. The NMR revealed none of the toluene reacted with the sulfenic acid 12 forming unwanted side products and nearly pure vinylglycine was obtained without any purification. The crude yield was close to the theoretical yield.

A sample of the vinylglycine was run on a chiral HPLC to obtain % ee. There was only one peak corresponding to vinylglycine using a Chiralpak™ AD column so the sample appeared initially to be optically pure.

Example 42

Preparation of Sulfides 18—General Procedure

To a suspension of bromide 17 (1 mmol), NaI (0.4 mmol), and K$_2$CO$_3$ (1 mmol) in dry acetone (10 mL) was added 1.05 mmol equiv of o-nitrothiophenol. The mixture was refluxed with stirring until the reaction was complete. The solution was then filtered, evaporated, redissolved in DCM, washed with brine, dried over Na$_2$SO$_4$, and concentrated. The sulfides 18 were purified by flash chromatography in accordance to product R$_f$ values.

Example 43

Benzyl 11-(2-nitrophenylthio)undecanoate (20b)

Yellow oil (670 mg, 88%); TLC (SiO$_2$) R$_f$ 0.48 (6:1 hexanes:EtOAc); $^1$H NMR (500 MHz, CDCl$_3$) δ 8.17 (dd, 1H, J=7.0, 1.5 Hz), 7.52 (dt, 1H, J=8.0, 1.5 Hz), 7.38 (d, 1H, J=8.0 Hz), 7.34-7.29 (m, 5H), 7.21 (dt, 1H, J=8.0, 1 Hz), 5.09 (s, 2H), 2.92 (t, 2H, J=7.5 Hz), 2.33 (t, 2H, J=7.5 Hz), 1.71 (qnt, 2H, J=7.5 Hz), 1.62 (qnt, 2H, J=7.5 Hz), 1.45 (qnt, 2H, J=7.5 Hz), 1.30-1.26 (m, 10H); $^{13}$C NMR (125 MHz, CDCl$_3$) δ 173.7, 146, 138.4, 136.2, 133.5, 128.6, 128.2, 126.7, 126.2, 124.3, 66.1, 34.4, 32.4, 29.4, 29.3, 29.2, 27.9, 25; ESI-HRMS calculated for C$_{24}$H$_{31}$NO$_4$S [M+H]$^+$ 430.2052, found 430.2041.

Example 44

S-Oxidation of Sulfides 18—General Procedure

To a stirring solution of sulfides 18a-18g (1 mmol) in DCM (10 mL) was added m-CPBA (1.25 mmol equiv) in 5 mL of DCM or in the case of disulfoxides 19h-19m, 2.50 equiv of peroxide was used. After 2.5 hr, the reactions were quenched with 5% NaHCO$_3$ (20 mL) and extracted twice with DCM. The combined organic extracts were dried over Na$_2$SO$_4$, filtered, and concentrated. The crude sulfoxides were purified by flash chromatography in accordance to product R$_f$ values.

Example 45

Benzyl 11-(2-nitrophenylsulfinyl)undecanoate (19b)

Yellow solid (532 mg, 74%); mp 37° C.-38° C.; TLC (SiO$_2$) R$_f$ 0.43 (3:1 hexanes:EtOAc); $^1$H NMR (500 MHz, CDCl$_3$) δ 8.31-8.28 (m, 2H), 7.93 (t, 1H, J=7.5 Hz), 7.68 (t, 1H, J=7.5 Hz), 7.32-7.28 (m, 5H), 5.09 (s, 2H), 3.15 (ddd, 1H, J=13, 9.5, 7.0 Hz), 2.72 (ddd, 1H, J=13.0, 9.5, 4.5 Hz), 2.32 (t, 2H, J=7.5 Hz), 2.02-1.95 (m, 1H), 1.63-1.58 (qnt, 2H, J=7.5 Hz), 1.51-1.46 (m, 1H), 1.41-1.35 (m, 1H), 1.30-1.24 (m, 10H); $^{13}$C NMR (125 MHz, CDCl$_3$) δ 173.8, 144.8, 144, 136.3, 135.5, 131.4, 128.7, 128.3, 126.9, 125.3, 66.2, 57.2, 34.4, 29.4, 29.4, 29.3, 29.2, 28.6, 25.2, 23.3; ESI-HRMS calculated for C$_{24}$H$_{32}$NO$_5$S [M+H]$^+$ 446.1996, found 446.2004.

Example 46

β-Elimination of ONP Sulfoxides (19)—General Procedure

Sulfoxide 19 (1 mmol equiv) and NaOAc (10 mmol equiv) were heated with stirring in toluene (10 mL) at 110° C. for 1-18 hrs. The solution was then cooled to RT and the precipitate removed by vacuum filtration through Celite. The flask was rinsed with toluene, filtered, and the solvent was evaporated to provide alkene 20. Decolorization of the concentrated product can be achieved by vacuum filtration of the oil through a plug of silica with 3:1 hexanes:EtOAc or for instances when starting material is still present, the mixture can be reheated in toluene with a fresh 10 equiv NaOAc until the reaction is complete.

Example 47

Benzyl undec-10-enoate (20b)

Colorless oil (28.2 mg, 86%); TLC (SiO$_2$) R$_f$ 0.40 (20:1 hexanes:EtOAc); $^1$H NMR (500 MHz, CDCl$_3$) δ 7.34-7.30 (m, 5H), 5.79 (ddt, 1H, ABM, J$_{BM}$=16.5, J$_{AM}$=10.5, 6.5 Hz), 5.10 (s, 2H), 4.98 (dd, 1H, ABM, J$_{BM}$=16.5, J$_{AB}$=1.5 Hz), 4.92 (dd, 1H, ABM, J$_{AM}$=10.5, J$_{AB}$=1.5 Hz), 2.34 (t, 2H, J=7.5 Hz), 2.02 (m, 2H), 1.63 (qnt, 2H, J=7.0 Hz), 1.36 (qnt, 2H, J=7.0 Hz), 1.28-1.25 (m, 8H); $^{13}$C NMR (125 MHz, CDCl$_3$) δ 173.7, 139.2, 136.2, 128.6, 128.2, 128.2, 114.2, 66.1, 34.4, 33.8, 29.3, 29.2, 29.1, 28.9, 24; ESI-HRMS calculated for C$_{18}$H$_{26}$O$_2$ [M+Na]$^+$ 297.1825, found 297.1826.

Example 48

Figures 14A, 14B:
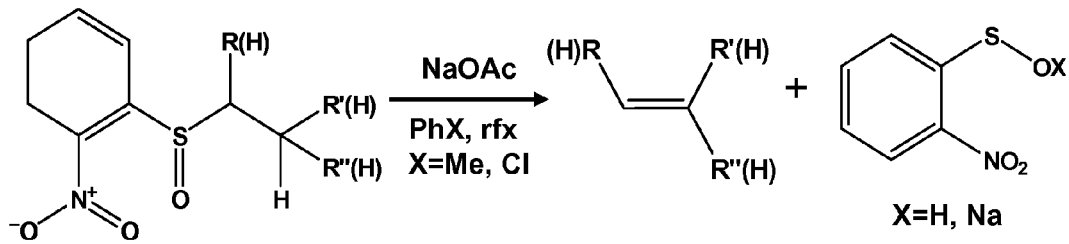
FIG. 14A is a schematic of a general method according to the disclosure for the synthesis of alkenes under mild thermolytic conditions.
FIG. 14B illustrates examples of alkenes formed by the reaction schematically presented in FIG. 13A.

The procedures of the disclosure can yield a wide variety of alkenes, depending on the substituents linked to the ONP-sulphoxide group. As shown in FIGS. 14A and 14B, for example, but not intended to be limiting as to the range of possible alkene products:

(a) An alkene having the general formula:

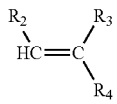

where R$_2$ is an alkyl group, such as a methyl, ethyl, propyl, and the like, or such as a branched alkyl groups. For example, R$_2$ is methyl and R$_3$ and R$_4$ are each hydrogen, the resulting alkene is propylene, as shown in FIGS. 14A and 14B.

(b) An alkene having the general formula:

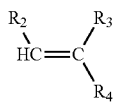

where R$_2$ is a phenyl, R$_3$ and R$_4$ are each hydrogen, and the product of the reaction in FIG. 14A is styrene.

(c) An alkene having the general formula:

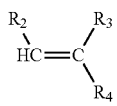

where R$_2$ is phenyl, or a substituted variant thereof, and R$_3$ and R$_4$ are both hydrogen, resulting a substitutes styrene. In the alternative, or in combination, R$_3$ may be such as an alkyl group, e.g., a methyl group to yield 3-methylstyrene and the like.

(d) An alkene having the general formula:

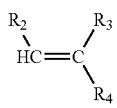

where R$_2$ is napthyl, or a substituted variant thereof, R3 is a phenyl, and R$_4$ is a phenyl or substituted phenyl. In these examples, the reaction as shown in FIG. 14A can yield an estrogen mimetic.

(e) An alkene having the general formula:

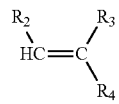

where R$_2$ and R$_4$ can each be independently a polycyclic aromatic hydrocarbon such as, but not limited to, an optionally substituted aromatic monocyclic or polycyclic hydrocarbon ring radical containing five to twenty carbon atoms (an acene). It is contemplated, however, that any aryl group in which an aromatic hydrocarbon ring is fused to one or more non-aromatic carbocyclic or heteroatom-containing rings, such as in an indanyl, phenanthridinyl or tetrahydronaphthyl, where the radical or point of attachment is on the aromatic hydrocarbon ring may be incorporated into the methods and reaction as shown in FIG. 14A. The "aryl" group can also positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl are, but are not limited to, phenyl, naphthyl, indenyl, azulenyl, fluorenyl, anthracenyl, phenanthrenyl, tetrahydronaphthyl, indanyl, phenanthridinyl and the like. Optional substituents include alkyl, aryl, aralkyl, heteroaryl, heteroaralkyl, cycloalkyl, heterocyclyl, halogen, haloalkyl, carboxy, carbamoyl, acyl, nitro, hydroxy, alkoxy, aryloxy, aralkyloxy, acyloxy, nitro, amino, and substituted amino.

In these examples, R$_3$ may be, but is not limited to H, Me, a halide, or OH. The final alkene product, therefore, can be, but is not limited to, a family of semiconductors as described, for example, in U.S. Pat. No. 7,315,042, incorporated herein in its entirety.

We claim:

1. A method for synthesizing an alkene, comprising:
   (a) providing a compound having formula III:

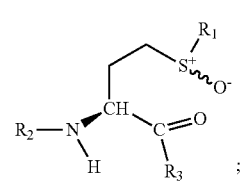

III wherein:
   R$_1$ is an electron withdrawing group, wherein said electron withdrawing group is an aryl group selected from the group consisting of: a phenyl group, a p-methoxyphenyl group, a p-chlorophenyl group, and an o-nitrophenyl group;
   R$_2$ is selected from the group consisting of: H, a carboxybenzyl group, an amino acid, and a peptide;
   R$_3$ is selected from the group consisting of: H, a methoxy group, an amino acid and a peptide;
   and wherein, if R$_2$ is an amino acid or a peptide, R$_3$ is a removable protecting group; and wherein, if R₃ is an amino acid or a peptide, R₂ is a removable protecting group;
(b) refluxing the compound having formula III in the presence of a non-polar aprotic solvent, and at a temperature of about 90° C. to about 135° C., thereby generating an alkene; and
(c) isolating from the non-polar aprotic solvent an alkene having formula:

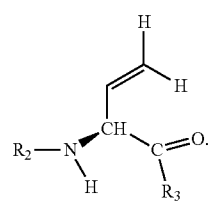

IV

2. The method of claim 1, wherein R₂ is carboxybenzyl, and R₃ is a methoxy group.
3. The method of claim 2, wherein the method further comprises deprotecting the compound having formula IV, thereby generating vinylglycine having formula V:

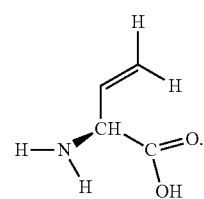

V

4. The method of claim 1, wherein R₁ is o-nitrophenyl.
5. The method of claim 1, wherein R₂ is an amino acid, and wherein R₃ is a methoxy group.
6. The method of claim 5, wherein R₂ is selected from the group consisting of: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.
7. The method of claim 1, wherein R₂ is carboxybenzyl, and wherein R₃ is an amino acid.
8. The method of claim 7, wherein R₃ is selected from the group consisting of: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.
9. The method of claim 1, wherein R₂ is a peptide, and wherein R₃ is a methoxy group.
10. The method of claim 1, wherein R₂ is carboxybenzyl, and wherein R₃ is a peptide.

11. The method of claim 1, wherein step (b) further comprises including with the non-polar aprotic solvent a molar excess of sodium acetate.
12. The method of claim 11, wherein the concentration of the sodium acetate is from about 10 equivalents to about 50 equivalents.
13. The method of claim 11, wherein the concentration of the sodium acetate is about 20 equivalents.
14. A compound having formula III:

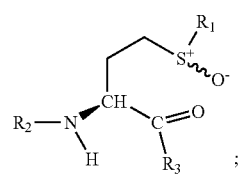

III wherein:
R₁ is an aryl group selected from the group consisting of: a phenyl group, a p-methoxyphenyl group, a p-chlorophenyl group, and an o-nitrophenyl group;
R₂ is selected from the group consisting of H, a carboxybenzyl group, an amino acid, and a peptide;
R₃ is selected from the group consisting of H, a methoxy group, an amino acid and a peptide;
and wherein, if R₂ is an amino acid or a peptide, R₃ is a removable protecting group; and
wherein, if R₃ is an amino acid or a peptide, R₂ is a removable protecting group.
15. The compound of claim 14, wherein R₁ is the aryl group o-nitrophenyl, R₂ is carboxybenzyl, and R₃ is a methoxy group, said compound having formula IV:

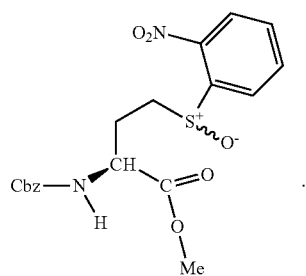

IV

16. The compound of claim 14, wherein if R₂ or R₃ is an amino acid, said amino acid is selected from the group consisting of: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

* * * * *